US009492250B2

(12) United States Patent
Gilles et al.

(10) Patent No.: US 9,492,250 B2
(45) Date of Patent: Nov. 15, 2016

(54) SUPPORT OF REMOVABLE COMPONENTS IN A TEETH MODEL MANUFACTURED BY MEANS OF CAM

(75) Inventors: Brieuc Gilles, Vanløse (DK); David Fischer, Stenløse (DK); Morten Markussen Lang, Stenløse (DK); Rune Fisker, Virum (DK); Sven Nonboe, Hillerød (DK); Steen Frost Tofthøj, Værløse (DK)

(73) Assignee: 3SHAPE A/S, Copenhagen K (DK)

( * ) Notice: Subject to any disclaimer, the term of this patent is extended or adjusted under 35 U.S.C. 154(b) by 542 days.

(21) Appl. No.: 13/580,822

(22) PCT Filed: Feb. 24, 2011

(86) PCT No.: PCT/DK2011/050057
§ 371 (c)(1),
(2), (4) Date: Oct. 2, 2012

(87) PCT Pub. No.: WO2011/103879
PCT Pub. Date: Sep. 1, 2011

(65) Prior Publication Data
US 2013/0041630 A1    Feb. 14, 2013

Related U.S. Application Data

(60) Provisional application No. 61/307,577, filed on Feb. 24, 2010, provisional application No. 61/375,346, filed on Aug. 20, 2010.

(30) Foreign Application Priority Data

Feb. 24, 2010   (DK) .................................. 2010 00151
Aug. 20, 2010   (DK) .................................. 2010 00730

(51) Int. Cl.
*G06G 7/48*       (2006.01)
*G06G 7/58*       (2006.01)
(Continued)

(52) U.S. Cl.
CPC ............. *A61C 13/0004* (2013.01); *A61C 9/00* (2013.01); *A61C 13/34* (2013.01); *A61C 9/002* (2013.01); *G06F 17/5018* (2013.01)

(58) Field of Classification Search
CPC .............. G06F 17/5018; A61C 9/002; A61C 13/0004; A61C 13/34; A61C 9/00
USPC ............... 703/11, 6; 433/201.1, 50; 700/103
See application file for complete search history.

(56) References Cited

U.S. PATENT DOCUMENTS

2001/0044092 A1    11/2001  Raffeiner
2004/0081938 A1*   4/2004   Chishti et al. .................. 433/24
(Continued)

FOREIGN PATENT DOCUMENTS

EP    1 119 308 B1    8/2007
EP    2 025 303 A1    2/2009
(Continued)

OTHER PUBLICATIONS

Lang, Lisa A. et al., "Finite Element Analysis to Determine Implant Preload", Dec. 2003, The Journal of Prosthetic Dentistry.*
(Continued)

*Primary Examiner* — Cedric D Johnson
(74) *Attorney, Agent, or Firm* — Buchanan Ingersoll & Rooney PC

(57) ABSTRACT

A computer-implemented method of generating a virtual model of a set of teeth for manufacturing a physical model of the set of teeth includes providing a virtual model of the set of teeth generating a cavity in said gingival part, into which cavity a removable component fits, where the removable component and the cavity are configured to provide a gap at an interface; and providing for supporting and positioning the removable component in the cavity, wherein the area of contact between the removable component and the cavity wall at the interface is controlled by the shape of the adjoining surfaces of the supporting and positioning and the other of the removable component and the cavity wall.

22 Claims, 15 Drawing Sheets

(51) Int. Cl.
*A61C 13/00* (2006.01)
*A61C 9/00* (2006.01)
*A61C 13/34* (2006.01)
*G06F 17/50* (2006.01)

(56) References Cited

U.S. PATENT DOCUMENTS

| | | | |
|---|---|---|---|
| 2007/0015111 A1 | 1/2007 | Kopelman et al. | |
| 2007/0128580 A1* | 6/2007 | Mormann | 433/201.1 |
| 2008/0299516 A1* | 12/2008 | Aldecoa | 433/174 |
| 2009/0047629 A1* | 2/2009 | Kim | 433/173 |
| 2009/0220916 A1 | 9/2009 | Fisker et al. | |
| 2010/0021859 A1* | 1/2010 | Kopelman | A61C 8/0001 433/50 |
| 2010/0159412 A1* | 6/2010 | Moss | A61C 7/002 433/24 |
| 2011/0196524 A1* | 8/2011 | Giasson | A61C 13/0004 700/103 |

FOREIGN PATENT DOCUMENTS

| | | |
|---|---|---|
| GB | 2 122 796 A | 1/1984 |
| WO | WO 00/19928 A1 | 4/2000 |
| WO | WO 2006/109176 A1 | 10/2006 |
| WO | WO 2009/017826 A1 | 2/2009 |

OTHER PUBLICATIONS

International Search Report (PCT/ISA/210) issued on May 16, 2011, by the Danish Patent Office as the International Searching Authority for International Application No. PCT/DK2011/050057.
Written Opinion of the International Searching Authority (Form PCT/ISA/237) dated May 16, 2011, issued in corresponding International Application No. PCT/DK2011/050057 (4 pages).
Danish Search Report issued on Sep. 24, 2010 for Application No. PA 2010 00151.
Danish Search Report issued on Mar. 17, 2011 for Application No. PA 2010 00730.

* cited by examiner

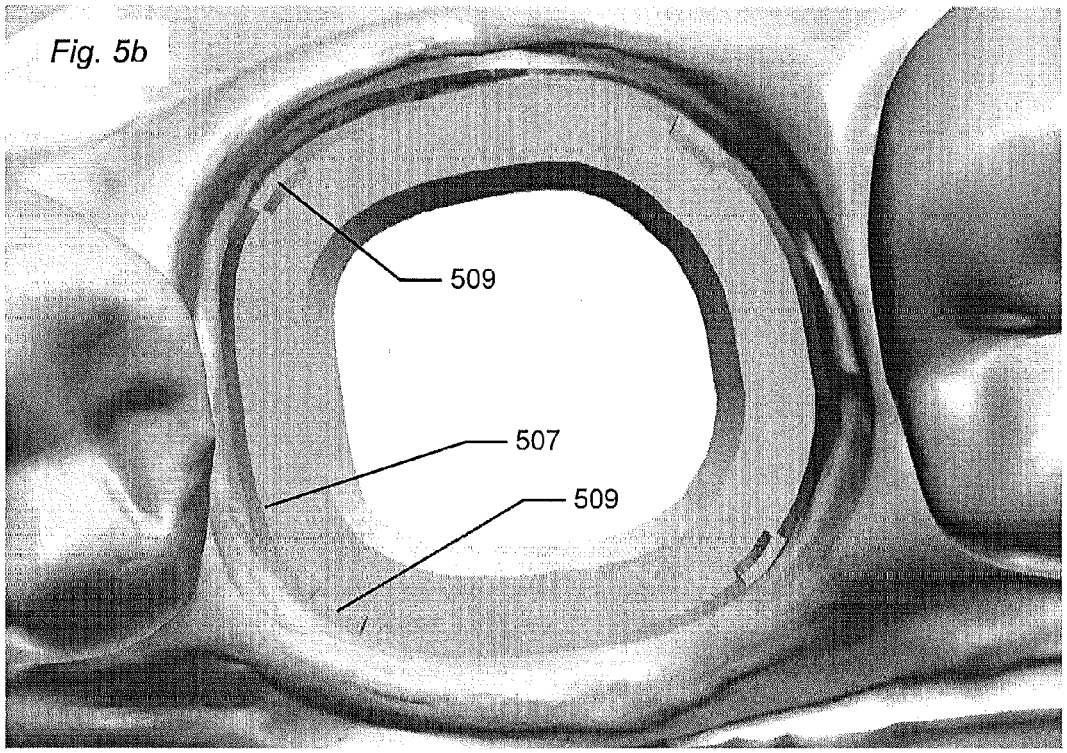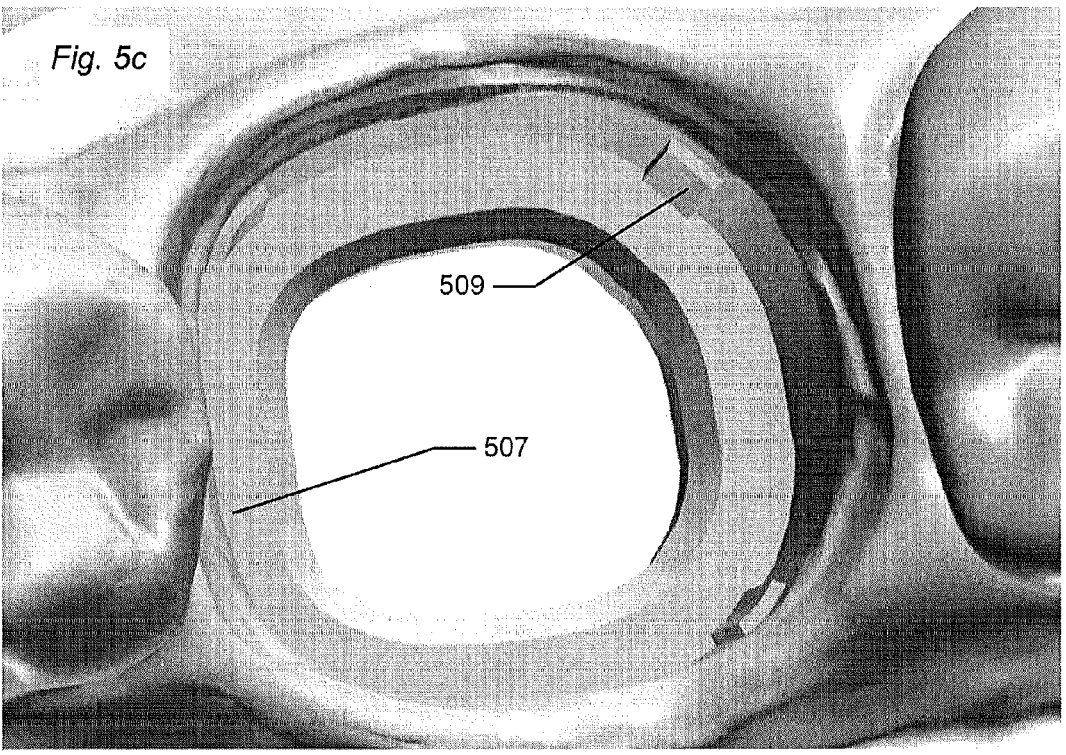

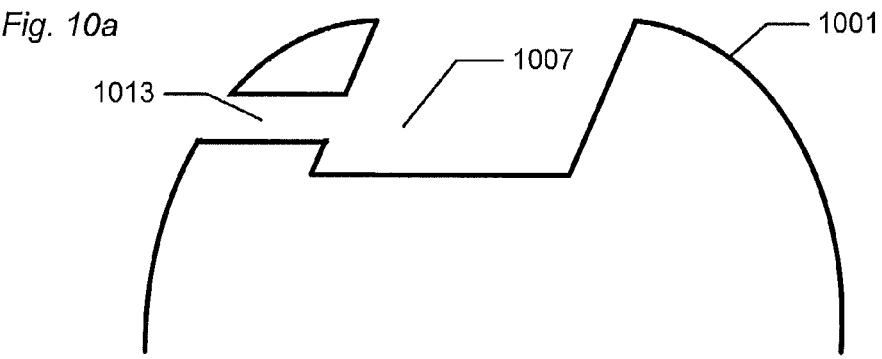
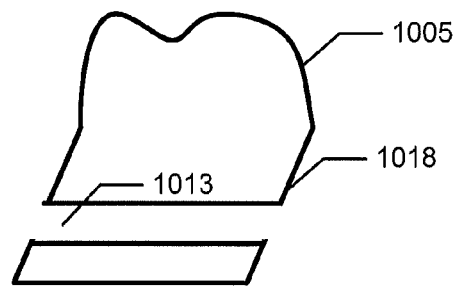
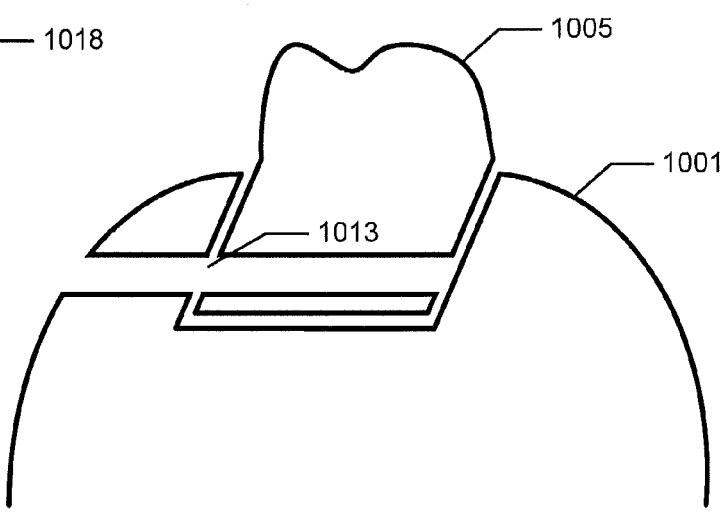
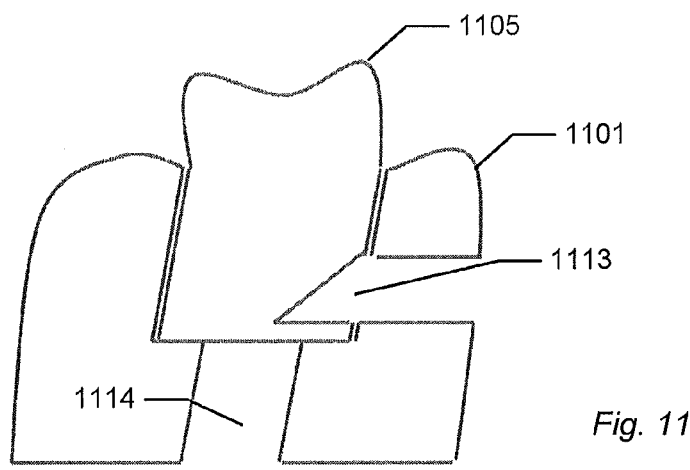

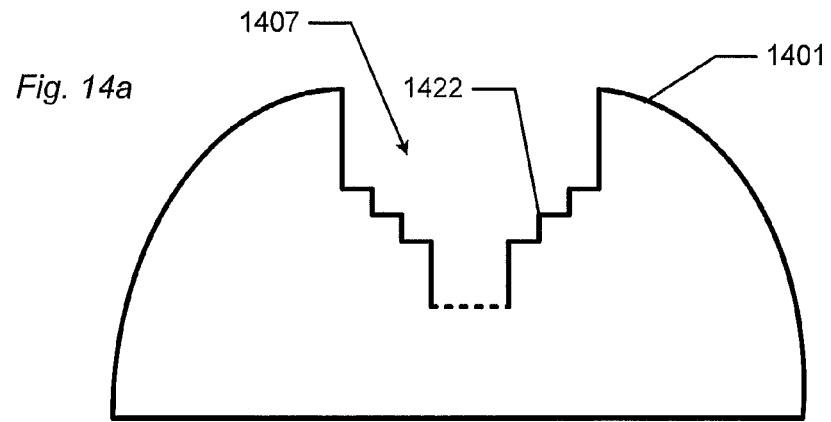
Fig. 14a
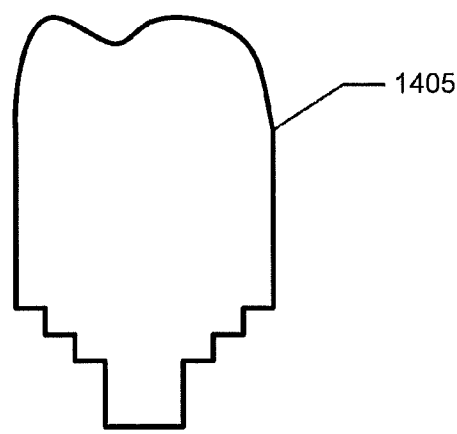
Fig. 14b
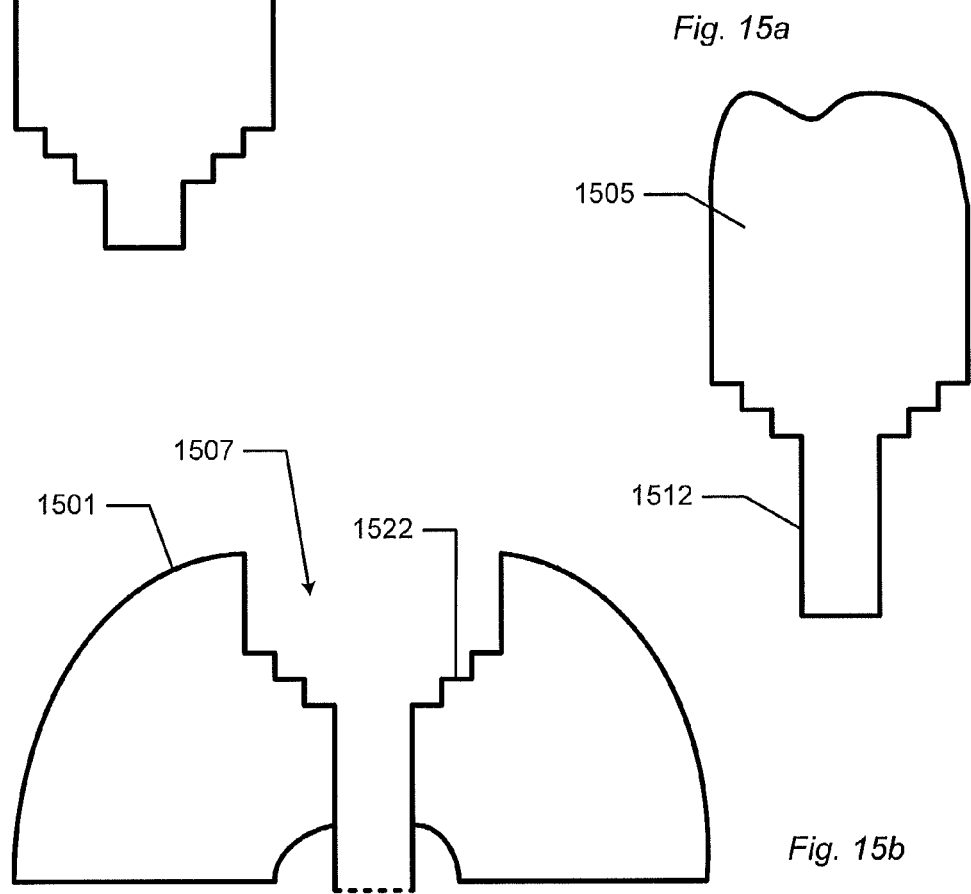
Fig. 15a
Fig. 15b

SUPPORT OF REMOVABLE COMPONENTS IN A TEETH MODEL MANUFACTURED BY MEANS OF CAM

BACKGROUND OF THE APPLICATION

This invention generally relates to a computer-implemented method of and a system for generating a virtual model of a set of teeth for manufacturing a physical model of the set of teeth, and to a physical model of a set of teeth.

DESCRIPTION OF RELATED ART

When a patient requires a dental restoration, such as crowns, bridges, abutments, or implants, the dentist will prepare the teeth e.g. a damaged tooth is grinded down to make a preparation where a crown can be glued onto. An alternative treatment is to insert implants, such as titanium screws, into the jaw of the patient and mount crowns or bridges on the implants. After preparing the teeth or inserting an implant the dentist can makes an impression of the upper jaw, the lower jaw and a bite registration or a single impression in a double-sided tray, also known as triple trays.

The impressions are sent to the dental technicians who manufacture the restorations. The first step to manufacture the restoration is traditionally to cast the upper and lower dental models from impressions of the upper and the lower jaw, respectively. The models are usually made of gypsum and often aligned in a dental articulator using the bite registration. The articulator simulates the real bite and chewing motion. The dental technician builds up the dental restoration inside the articulator to ensure a nice visual appearance and bite functionality. A proper alignment of the cast in the articulator is crucial for the final restoration.

CAD technology for manufacturing dental restorations is rapidly expanding improving quality, reducing cost and facilitating the possibility to manufacture in attractive materials otherwise not available. The first step in the CAD manufacturing process is to create a 3D virtual model of the patient's teeth. This is traditionally done by 3D scanning one or both of the dental gypsum models. The 3D replicas of the teeth are imported into a CAD program, where the entire dental restoration, such as a bridge substructure, is designed. The final restoration 3D design is then manufactured e.g. using a milling machine, 3D printer, rapid prototyping manufacturing or other manufacturing equipment. Accuracy requirements for the dental restorations are very high otherwise the dental restoration will not be visual appealing, fit onto the teeth, could cause pain or cause infections.

US2009220916 relates to a method for obtaining an accurate three-dimensional model of a dental impression, said method comprising the steps of, scanning at least a part of an upper jaw impression and/or a lower jaw impression, obtaining an impression scan, evaluating the quality of the impression scan, and use the impression scan to obtain a three-dimensional model, thereby obtaining an accurate three-dimensional model of the dental impression.

GB 2122796 discloses a teeth model made from a base (10) of resiliently deformable rubberised material in the shape of a gum which includes a groove (12) into which pegs of removable individual tooth models (14) are fitted. Each peg (14) includes shoulders (20, 22) and the groove has lateral protrusions (30, 32) for cooperating therewith so that each peg has to be forced into the slot past the protrusions so as to be retained in position. The natural resilience of the material forming the imitation gum is such as to allow the teeth to be removed by forcing each tooth out of the slot thereby deforming the protrusion. Each tooth is individually removable from the imitation gum, and whilst the visible crown of each tooth differs according to normal anatomy the peg of each tooth is identical thus providing a student with no indication as to the correct position for each tooth.

US 2001044092 discloses that a dental model, in particular for practice purposes, is provided, and has a support plate with recesses for artificial teeth, each of which has a tooth stump that fits into the associated recess. A gum mass overlaps both the teeth of a row of teeth and the recesses. The teeth are each disengageably held on the plate and in their associated recess with friction.

EP1119308B discloses a computer-implemented method for use in developing a course of treatment for an orthodontic patient, the method comprising: obtaining a digital model of a patient's dentition, including a dental model representing the patient's teeth at a set of initial positions and a gingival model representing gum tissue surrounding the teeth; and deriving from the digital model an expected deformation of the gum tissue as the teeth move from the initial positions to another set of positions.

It remains a problem to provide an alternative and more efficient method for generating a virtual model of a set of teeth comprising a tooth which requires a restoration and/or a dental treatment, and for generating a physical model of the set of teeth comprising such a tooth, such that the dental technician can test the dental restorations, e.g. a crown, on the physical model.

SUMMARY OF THE DISCLOSURE

Disclosed is a computer-implemented method of generating a virtual model of a set of teeth for manufacturing a physical model of the set of teeth, where the method comprises:
  providing a virtual model of the set of teeth, the model comprising a gingival part and a tooth configured to be part of a removable component in the model;
  generating a cavity in said gingival part, said cavity comprising a cavity wall, into which cavity the removable component fits such that an interface between the removable component and the cavity wall is defined, where the removable component and the cavity are configured to provide a gap at said interface; and
  providing means for supporting and positioning the removable component in the cavity, where the means for supporting and positioning are generated on one of said removable component and said cavity wall such that the means for supporting and positioning extends across said gap between said removable component and said cavity wall, such that in a physical model manufactured from the virtual model, the means for supporting and positioning support and position the removable component in the cavity;
wherein the area of contact between the removable component and the cavity wall at said interface is controlled by the shape of the adjoining surfaces of the means for supporting and positioning and the other of the removable component and the cavity wall.

The means for supporting and positioning may extend locally across said gap between said removable component and said cavity wall, i.e. the at some parts of the circumference of the removable component the gap may be closed by the means for supporting and positioning, while at other parts of the circumference, the gap is still open.

In some embodiments, said means for supporting and positioning comprises supporting elements. In a physical model manufactured from the virtual model the supporting elements may extend across said gap between said removable component and said cavity wall such that it is the supporting elements which support and position the removable component in the cavity.

Disclosed is a computer-implemented method of generating a virtual model of a set of teeth for manufacturing a physical model of the set of teeth, where the model comprises one or more teeth preparations, where the method comprises:

generating a virtual model of the set of teeth, where the virtual model is based on the virtual representation of the set of teeth;

providing that each of the teeth preparations is configured to be arranged as a removable component in the model, where each removable component is adapted to fit into a corresponding cavity in the gingival part of the model;

providing means for supporting and positioning each of the removable components in their corresponding cavities in the model.

The method further comprises the step of:

configuring the means for supporting and positioning such that the area of contact between each removable component and its corresponding cavity is smaller than the area in which there is no contact between the removable component and the cavity.

Disclosed is a computer-implemented method for improving a virtual model of a set of teeth, the method comprising:

providing a virtual model of a set of teeth, said model comprising a gingival part and at least one tooth configured to be part of a removable component, wherein a cavity corresponding to the removable component is defined in said gingival part, said cavity comprising a cavity wall, wherein the removable component is adapted to fit into the cavity such that an interface between the removable component and the cavity wall is defined; and improving the virtual model by providing means for supporting and positioning on one of said removable component and said cavity wall such that in a physical model manufactured from the virtual model, the means for supporting and positioning extends across said gap between said removable component and said cavity wall such that the means for supporting and positioning support and position the removable component in the cavity;

wherein the area of contact between the removable component and the cavity wall at said interface is controlled by the shape of the adjoining surfaces of the means for supporting and positioning and the other of the removable component and the cavity wall, the means for supporting and positioning allowing for a controlled reduction of the area of contact in a physical model manufactured from the improved virtual model compared to a physical model formed from a virtual model without said means for supporting and positioning.

Disclosed is a system for generating a virtual model of a set of teeth for manufacturing a physical model of the set of teeth, where the system comprises:

means for generating a virtual model of the set of teeth, where the virtual model is based on a virtual representation of the set of teeth;

means for providing that at least one tooth is configured to be arranged as part of a removable component in the model, where the removable component is adapted to fit into a corresponding cavity in the gingival part of the model such that an interface between the removable component and a wall of the cavity is defined, where the removable component and the cavity are configured to provide a gap at said interface;

means for providing means for supporting and positioning each removable components in their corresponding cavities in the model, where the means for supporting and positioning are provided on one of said removable component and said cavity wall such that the means for supporting and positioning extends across said gap between said removable component and said cavity wall; and means for configuring the means for supporting and positioning such that the area of contact between the removable component and the cavity wall at said interface is controlled by the shape of the adjoining surfaces of the means for supporting and positioning and the other of the removable component and the cavity wall.

Disclosed is a physical model of a set of teeth, the physical model comprising at least one tooth; and a gingival part, wherein a cavity is defined, said cavity comprising a cavity wall;

wherein said tooth is configured to be part of a removable component adapted to fit into the cavity in said gingival part such that an interface between the removable component and the cavity wall is provided; and wherein on one of said removable component and said cavity wall comprise means for supporting and positioning, such that in a physical model manufactured from the virtual model, the means for supporting and positioning extends across said gap between said removable component and said cavity wall such that the means for supporting and positioning support and position the removable component in the cavity;

wherein the area of contact between the removable component and the cavity wall at said interface is controlled by the shape of the adjoining surfaces of the means for supporting and positioning and the other of the removable component and the cavity wall.

Disclosed is a physical model of a set of teeth, wherein the physical model is manufactured from a virtual model generated by the method according to the present invention.

In the context of the present disclosure the phrase "configured to be a removable component in the model" may refer to the situation where the tooth can be removed from the model (virtual and/or physical) and subsequently can be inserted into the model again. A tooth may be comprised in the removable component, such that the removable component may comprise the tooth and a base. The removable component may consist of a tooth. The removable component may be removable from the gingival part of the model. The removable component may be attached to the gingival part of the model by the friction between the removable element and the cavity wall.

In the context of the present disclosure, the phrase "the base of the removable component" may be used interchangeably with the phrase "the bottom part of the removable component".

In the context of the present disclosure, the phrase "the model" may be used in relation to both the physical and the virtual manifestation of the set of teeth. In some embodiments, there is a one-to-one relationship between the virtual model and the physical model of the set of teeth.

In some embodiments, at least part of said means for supporting and positioning are generated on the removable component such that the area of contact between the removable component and the cavity wall at said interface is controlled by the shape of the adjoining surfaces of the means for supporting and positioning and the cavity wall.

In some embodiments, at least part of said means for supporting and positioning are generated on the cavity wall such that the area of contact between the removable component and the cavity wall at said interface is controlled by the shape of the adjoining surfaces of the means for supporting and positioning and the removable component.

The means for supporting and positioning generated on the cavity wall and/or on the removable component may be an integral part of the unit on which they are generated such that e.g. a supporting element becomes a part the structure on which it is generated.

The tolerance with regard to position of and space between the removable component and the gingival part of the model must be very precise, so that the removable component fits perfect into the cavity of the model.

Consequently, it may be an advantage that by providing the means for supporting and positioning, the removable components only rest at few points in the cavity and does not rest on or contact the entire inner surface of the cavity. Thus it may be an advantage that it is easier and more reliably to provide the removable components to fit perfect into the cavity, without being too firmly attached or too loosely attached.

The means for supporting and positioning may keep the removable component in place in the cavity, such that the removable component does not move or relocate within the cavity. Hereby the removable component is fixedly attached within the model when a dental technician e.g. is using the model for adjusting dental restorations.

It may be an advantage that the removable component does not have full contact with the cavity, but only partly contact in certain few areas or regions. Thus there is a gap between the removable component and the cavity, except at the points where the means for supporting and positioning are arranged, here there is contact.

In the context of the present disclosure, the phrase "the wall of the cavity" or the equivalent "the cavity wall", may refer to the part of the inner surface of the cavity, which is substantially parallel to the longitudinal direction of the removable component and/or of the cavity itself. The cavity wall may be the part of the inner surface of the cavity along which the removable component is moved when placing it in or removing it from the cavity.

The cross sectional shape of the cavity may be rounded such that the cavity wall comprises one coherent surface which forms the entire cavity wall.

The cross sectional shape of the cavity may comprise corners each connecting two parts of the cavity wall, such as in a cavity comprising several sides which together forms the cavity wall. The cavity may e.g. have a rectangular cross section with four sides which together form the cavity wall.

The contact may be between the surface, e.g. the inner surface, of the cavity and the surface, e.g. the outer or external surface, of the removable component.

The inner surface may be the wall of the cavity and maybe also the bottom of the cavity.

The physical model can be used as a working model when a dental technician is fitting, testing, adjusting a dental restoration for a patient. A part of the removable component may thus be shaped as a tooth, which is prepared for a dental restoration, thus the teeth preparations are originally teeth prepared for a dental restoration, such as a bridge, a crown etc.

In the context of the present disclosure, the phrases "bottom" and "top" may refer to two opposite ends of a part of the model. For instance, a removable component may comprise a bottom part and a top part, wherein the phrase "bottom part" may refer to the part of the removable component which is inserted into its corresponding cavity thereby defining an interface between cavity and removable component. The "top part" of the removable component may be the part which is visible when the removable component is inserted into its corresponding cavity. The phrases "top" or "bottom" are only used to describe the relative orientation of the parts of the model and does not present a limitation on which part is closer to the ground than the other parts. The opening though which the removable component enters the cavity may also be located closer to the ground than the bottom of the cavity or vise versa.

In some embodiments the ratio between the area of contact and the area of said cavity wall is below about 0.9, such as below about 0.8, such as below about 0.7, such as below about 0.6, such as below about 0.5, such as below about 0.4, such as below about 0.3, such as below about 0.2, such as below about 0.1, such as below about 0.05, such as below about 0.02.

In some embodiments the ratio between the area of contact and the area of said interface is below about 0.9, such as below about 0.8, such as below about 0.7, such as below about 0.6, such as below about 0.5, such as below about 0.4, such as below about 0.3, such as below about 0.2, such as below about 0.1, such as below about 0.05, such as below about 0.02.

In some embodiments the area of contact for one supporting element is in the range of about 0.01 mm$^2$ to about 40 mm$^2$, such as in the range of 0.1 mm$^2$ to about 20 mm$^2$, such as in the range of 0.5 mm$^2$ to about 10 mm$^2$.

In some embodiments the width of said supporting element in said area of contact is in the range of about 0.01 mm to about 4 mm, such as in the range of about 0.1 mm to about 2 mm.

In some embodiments the length of said supporting element in said contact area is in the range of about 0.01 mm to about 20 mm, such as in the range of about 0.1 mm to about 10 mm.

In some embodiments, the height of the supporting elements is in the range of about 0.05 mm to about 2 mm, such as in the range of about 0.1 mm to about 1.5 mm, such as in the range of about 0.2 mm to about 1 mm.

In the context of the present disclosure, the phrase "the width of a supporting element" may refer to the cross sectional dimension of the supporting element along the interface between the removable component and the cavity wall.

In the context of the present disclosure, the phrase "the length of a supporting element" may refer to the longitudinal dimension of the supporting element.

In the context of the present disclosure, the phrase "the height of a supporting element" may refer to the cross sectional dimension of the supporting element across the gap at the interface between the removable component and the cavity wall, i.e. perpendicular to the surface of the removable component and/or of the cavity wall.

In some embodiments, the contour of the cavity wall and the contour of the removable component are parallel, thus there is a constant distance between the contours. In such embodiments there is a constant distance between the removable component and the cavity wall except at the supporting elements, where the supporting elements provide a contact between the two.

In the context of the present disclosure, the phrase "the longitudinal direction" may refer to the insertion direction of the removal component in the gingival part of the model.

In the context of the present disclosure, the phrase "cross sectional" may refer to a plane which is perpendicular to the longitudinal direction. The cross sectional shape of e.g. a base of a removable element may be the shape of the base in such a plane intersecting the base.

In some embodiments, said means for supporting and positioning are generated on said cavity wall. In some embodiments, said means for supporting and positioning are generated on said removable component. In some embodiments, means for supporting and positioning are defined on both the cavity wall and on the removable component.

Disclosed is a computer-implemented method of generating a virtual model of a set of teeth, where the virtual model is based on a virtual representation of the set of teeth, where the virtual model is adapted to be used for manufacturing a physical model of the set of teeth, where the method comprises:

providing that one or more teeth of the virtual model are configured to be arranged as one or more removable components in the physical model, providing means for supporting and positioning each of the removable components in the physical model.

In some embodiments, a cavity is formed in a gingival part of the model, said cavity comprising a cavity wall, where said means for supporting and positioning are generated on one of the removable component and the cavity wall, such that the means for supporting and positioning extends across said gap between said removable component and said cavity wall, where the area of contact between the removable component and the cavity wall at said interface is controlled by the shape of the adjoining surfaces of the means for supporting and positioning and the other of the removable component and the cavity wall.

In some embodiments, said tooth comprises a tooth which requires a restoration and/or a dental treatment, and for generating a physical model of the set of teeth comprising such a tooth, such that the dental technician can test the dental restorations, e.g. a crown, on the physical model.

In some embodiments the means for supporting and positioning, such as the supporting elements, is at least partly shaped so that it resembles the shape of the surface of the removable component at the interface and/or the shape of the cavity wall.

The shape may be defined as an anatomical shape.

The supporting elements may be shaped so that in the contact area, the surfaces of the supporting elements and the removable component are parallel. The supporting elements may be shaped so that in the contact area, the surfaces of the supporting elements and the cavity wall are parallel. The shape of the supporting elements may follow the shape of the one of the removable component and the cavity wall on which they are generated.

In some embodiments the means for supporting and positioning comprises one or more friction points providing friction between the removable component and the cavity.

An advantage of this embodiment is that friction points will serve well as means for supporting and positioning, because they will keep the removable component in place in the cavity, such that the removable component does not move or relocate within the cavity. Furthermore, the friction points may be easy to provide virtually and manufacture. Thus the friction is created due to that the removable component and friction points overlap each other a small distance, e.g. a few millimeters.

In some embodiments, the supporting element comprises one or more friction points providing friction between the removable component and the cavity.

The supporting elements are configured such that they cover only a fraction of the interface between the removable component and the cavity such that the contact area and hence the friction between the removable component and the cavity wall is reduced compared to a physical model wherein the contact area is substantially identical to the area of the interface thus resulting in an easier removal of the tooth from the gingival part of a physical model manufactured from the virtual model.

The supporting elements, such as friction points, may provide a controlled reduction of the friction between the removable component and the cavity.

In some embodiments the supporting elements are arranged in positions corresponding to each substantially straight side of the base of the removable component.

In some embodiments the supporting elements are arranged in positions corresponding to corners of the base of the removable component.

In some embodiments the supporting elements are arranged such that two supporting elements are substantially opposing each other.

In some embodiments the supporting elements are arranged such that two supporting elements are arranged substantially on opposite sides of or relative to the removable component.

In the context of the present disclosure, the phrase "arranged on opposite sides of or relative to the removable component" may refer to the case where e.g. first and second supporting elements are arranged on an opposite of the removable component relative to a central part of the removable component. On a removable component comprising a circular base, the phrase may refer to the situation where the first and second supporting elements are diagonally arranged, such that a line connecting the first and second supporting elements passes through the center of the base. On a removable component comprising a rectangular base, the phrase may refer to the situation, where the first and second supporting elements are arranged on opposing surfaces of the base.

An advantage of this embodiment is that when supporting elements are arranged opposite each other, they may provide a very firm attachment of the removable component in the cavity.

In some embodiments the supporting elements are arranged with an equidistant distance to each other.

In some embodiments the distance is measured along the inner surface of the cavity or the outer surface of the removable component.

In some embodiments the supporting elements are formed as cut-off pyramids or as square frusta or rectangular frusta.

An advantage of the embodiments is that the friction or the supporting elements are created due to that the removable component and the cut-off pyramids overlap a small distance, e.g. a few millimeters.

In some embodiments, the cut-off pyramids, or the square frusta or the rectangular frusta are arranged with the broadest part arranged at the surface of the cavity and the narrowest part pointing towards the position, where the removable component is configured to be arranged.

In some embodiments, the cut-off pyramids or square frusta or rectangular frusta are arranged with the broadest part arranged at the one of said removable component and said cavity wall on which they are generated, and with the narrowest part at the contact area to the other of said removable component and said cavity wall.

In some embodiments a number $N_{elem}$ of supporting elements are provided on the removable component and/or the cavity wall. The number $N_{elem}$ may be selected from the group of 3, 4, 6, 8, 9, 10, 12 or 16.

In some embodiments the method comprises providing 3 friction points, 4 friction points, 6 friction points, 8 friction points, 9 friction points, 10 friction points, 12 friction points, 16 friction points or more friction points.

In some embodiments, the model comprises a removable component which comprises one, two or more teeth.

In some embodiments, the model comprises two or more removable components. Each of the removable components may comprise one or more teeth In some embodiments, the contour of the cavity wall follows an outer curve and the contour of the removable component follows an inner curve, where the inner curve is arranged inside the outer curve.

The inner curve and the outer curve may be substantially parallel such that said gap has a substantially constant width along the contours except at the positions, where the means for supporting and positioning extend across said gap and close it.

In some embodiments, supporting elements generated on said removable component comprise a surface in the contact area which is substantially aligned with the outer curve, such that these supporting elements are shaped to have a surface in the contact area which is parallel to the surface of the cavity wall at the contact area.

In some embodiments, supporting elements are generated on in the wall of said cavity and comprise a surface in the contact area which is substantially aligned with the inner curve, such that these supporting elements are shaped to have a surface in the contact area which is parallel to the surface of the removable component at the contact area.

In some embodiments there is a constant distance from the part of the supporting element pointing towards the position of the removable component to the surface of the cavity.

Alternatively the distance is not constant, e.g. if the shape of the means for supporting and positioning does not follow the contour of the cavity, but is e.g. a straight line disregarding the anatomical shape.

In some embodiments the method comprises providing four friction points.

In some embodiments the method comprises providing a pin at the base of each removable component, where the pin is shaped so that its cross sectional shape resembles the cross sectional shape of the base of the removable component, where the cross sectional dimension of the pin is smaller than the cross sectional dimension of the base of the removable component The shape may be defined as an anatomical shape.

An advantage of this embodiment is that when e.g. printing the physical model, there is a need for supporting the large regions of the model, but traditional supports, e.g. being thin or small, can deteriorate the quality of the edge of the removable component resting in the cavity of the model. By providing that the geometry of the support pin is adapted to the shape of the removable component, the traditional or conventional supports can be avoided on that edge and thereby the risk of faults is reduced.

The larger the pin is the less may the risk be that it will break.

In some embodiments, the method comprises providing a virtual representation of a set of teeth and forming a virtual model of said set of teeth from said virtual representation.

In some embodiments the virtual representation of the set of teeth is provided by scanning the set of teeth by means of an intraoral scanner or scanning an impression of the set of teeth. The virtual representation of the set of teeth may comprise a point cloud.

Thus the virtual model and afterwards the physical model may be created based on scanning e.g. an impression instead of e.g. creating a model by casting the model from an impression. An advantage of this embodiment is that better accuracy is obtained, because the impression itself is scanned instead of scanning a casted or poured model, in which defects may have emerged, when making the model. Furthermore, it may be an advantage that the manual and time consuming work of making the model in gypsum from the impression is avoided. Thus this embodiment provides a simpler and possibly faster and cheaper process.

A reason for manufacturing a physical model from the impression is that dental technicians may prefer to have a physical model to work with when they adapt the dental restoration(s) for a patient.

An advantage of this embodiment is that the impression can be scanned to create a representation of both the lower and upper part of the jaws.

An advantage of this embodiment is that the virtual model is automatically generated in software based on the scanning of the impression.

In some embodiments the method comprises defining a curve on the virtual model and removing everything of the model from visualisation which is outside this curve.

An advantage of this embodiment is that it enables that only the part of the model which the user wishes to work with, and not the entire model, is visualised, e.g. seen or shown on a screen.

In some embodiments the method comprises automatically defining a margin line for a removable component based on the centre of mass of the removable component.

In some embodiments the method comprises automatically removing neighbor teeth in the direction of view such that a user is able to have an unspoiled view of the model for editing a margin line.

In some embodiments the method comprises removing some of the part of the model corresponding to the gingiva, such that it becomes easier for a user to take the removable component out of the physical model.

In some embodiments the method comprises defining a cylinder corresponding to an insertion direction such that it can be checked if the neighbor teeth are affected when taking the removable component in or out of the model.

In some embodiments the method comprises applying a scan of the entire set of teeth so that the antagonist is visualized, and providing a virtual articulator, so that the entire set of teeth can be occlusion tested.

In some embodiments the method comprises manufacturing the physical model by means of three dimensional printing or milling.

Examples of 3D printing or milling are:
inkjet-like principle, where it is possible to manufacture the outer part of the physical model in a high quality and/or an expensive material, and the inner part can be manufactured in a cheaper material, such as e.g. wax;
standard 3D printing;
standard 3D milling;
steriolithography (SLA), which is a type of rapid prototyping process;

selective laser sintering (SLS), which is a type of rapid prototyping process.

In some embodiments the method comprises designing and adapting the model to be manufactured by means of a specific manufacturing process.

For example different materials can be chosen for manufacturing of the physical model.

In some embodiments the method comprises designing perforations or openings in the gingival part of the model pointing away from the removable components such that fluid used in the manufacturing process is allowed to run out of the model in order to decrease the amount of material to be used. Thus the model may be hollow and consists of just a shell. An advantage of this embodiment is that if the material shrinks and there is less material, there will be less shrinking and thus less defect of the model.

In some embodiments the method comprises defining connectors for connecting a model of teeth in an upper jaw and a model of teeth in a lower jaw such that the two models are adapted to be attached to each other in an anatomically correct way.

In some embodiments the method comprises that the removable component and the means for supporting and positioning are manufactured such that the removable component is positioned anatomically correct in the physical model corresponding to the position of the real, anatomical teeth in the mouth of the patient.

A removable component may also be denoted a tooth, a tooth preparation, a die etc.

In some embodiments the method comprises providing that the shape of the visible part of the removable component in the model corresponds to the visible part of the real, anatomical tooth, when the removable component is arranged in its correct anatomical position in the physical model, whereby no gingiva is part of the removable component.

In some embodiments the correct anatomical position of the removable component is with regard to the height relative to the model, with regard to the horizontal position which can be controlled by ensuring that the removable component cannot rotate when placed in the model and/or with regard to the friction between the removable component and the corresponding cavity in the model.

When the removable component is arranged to have an anatomical correct height relative to the gingival part of the model, the tooth of the removable component may be arranged correctly relative to the horizontal plane of the teeth model. When the removable component is arranged correctly with regard to the friction between the removable component and the cavity, it may be arranged such that the relative position of the supporting elements and the removable component/the cavity wall is such that the supporting elements provide a correct friction.

The physical model of the set of teeth may be used by a dental technician to build up a model of the restoration, which may be known as the wax modulation. The model of the restoration or the wax modulation may then be used to cast the actual restoration, which is for example made of a metal material, such as a metal crown with porcelain veneering.

The physical model may be used to check whether a manufactured restoration actually fits the physical removable component in the physical model.

Even if the restoration is produced by CAD/CAM, it is still advantageous to check that the produced restoration has a correct fit by checking the restoration on the physical model. There are several steps in the manufacturing process, so potentially something could go wrong in one of the steps, and then it is better that the dental technician discovers and corrects a fault before the restoration is send to the dentist and inserted in the patient's mouth.

If the restoration is produced from a material which can change shape or size, e.g. zirconium dioxide also known as zirconia, it is also an advantage to check the restoration after production, because the material may then shrink or become crooked during and/or after the heating process.

If the restoration is produced manually and/or when the porcelain work on the restoration is performed manually, then the dental technician needs a model of the other teeth in the set of teeth to check that there is space enough between the neighbor teeth for the restoration and that the shape of the porcelain match the neighbor teeth.

If the model is manufactured by 3D printing, many models can be manufactured simultaneously compared to fx manufacturing by milling.

The method may comprise that at least one tooth is not removably inserted in the physical model i.e. the tooth can not be removed from the model but is manufactured as part of the model, and is therefore fixed in the model.

The method may comprise that at least one tooth is manufactured as fixed part of a coherent structure comprising the gingival part and the fixed tooth, such that the fixed tooth can not be removed from the gingival part.

This may be an advantage when fabricating veneers in a lab, since hereby it may not be necessary to remove the tooth from the model. Furthermore, it may be an advantage to control the restoration in a completely inflexible model with no removable component, since this may provide a very good control.

In some embodiments the method comprises that the removable components are manufactured to have no pins.

It may be an advantage that by manufacturing the physical model with cavities for the removable components, pins may be omitted from the removable components, and this may be an advantage since pins may be likely to brake of from the removable components, and pins may hinder or obstruct a perfect fit of the removable components in the model, etc.

Furthermore, if manufacturing a removable component and the model by solidifying a liquid layerwise, it may be difficult to produce a pin, since the stop surface on the rest of the removable component is not carried or supported by anything as it is being produced in the liquid.

In some embodiments the method comprises digitally repositioning the gingival part of the model around the removable component, before manufacturing the model.

This repositioning may be an advantage because often it is a problem that when a tooth is prepared in the mouth of the patient, then so much of the tooth is grinded away, whereby the soft, compliant gingival tissue around the prepared tooth will adjoin or follow or collapse to the new reduced shape of the prepared tooth instead of remaining in the original shape following the non-prepared tooth. So when e.g. the impression of the prepared tooth is made, then the gingiva is adjoining the prepared tooth and the manufactured model of the teeth will then have a gingiva adjoining the removable component, and thus there may be no space between the gingival and the removable component to model and place a restoration. But when repositioning, removing, or relocating the gingival part of the model around the removable component then there is space for the restoration and the veneering, e.g. porcelain, which the dentist may add after having inserted the restoration in the mouth of the patient.

In some embodiments, digitally repositioning the gingival part of the model comprises digitally moving the gingival part of the model away from to the removable component.

The digital repositioning the gingival part of the model may comprise moving the gingiva adjoining the removable component.

In some embodiments digitally repositioning the gingival part of the model comprises digitally moving the gingival part of the model outwards relative to the removable component.

It may be an advantage that the gingival part of the model may be moved without changing the size of gingiva, which is important since the gingival in the mouth of the patient also will only change shape and move but not change size, i.e. the gingival does not become bigger or smaller, it only changes shape.

It may be an advantage that if the model of the restoration is designed using CAD, then it can be derived from the CAD program how much the gingiva on the teeth model should be moved in order to fit the modeled restoration.

In some embodiments the method comprises that the teeth of the model is manufactured in a hard, non-flexible material and at least the gingival of the model around the removable component is manufactured in a soft, flexible material.

In some embodiments the method comprises that the teeth of the model are manufactured in a relatively harder, less flexible material and at least the gingival of the model around the removable component is manufactured in a relatively softer, more flexible material.

It may be an advantage to manufacture the teeth of the model in a relatively harder material and the gingival part of the model in a relatively softer material, because then the different materials resemble the real materials in the mouth, and this facilitates the testing or modeling of the restoration.

In some embodiments the shape of the supporting elements in a plane defined by the interface are bars, squares, ovals, stars, or triangles.

In some embodiments the method comprises that the volume of a supporting element generated on the cavity wall is manufactured to overlap at least partly with the volume of the removable component, when the removable component is arranged in the cavity, such that a tight fit is created between the cavity and the removable component.

In some embodiments, the volume of a supporting element generated on a removable component is manufactured to overlap at least partly with the volume of the cavity wall, such that when the removable component is arranged in the cavity a tight fit is created between the cavity and the removable component.

In some embodiments, the volume of a supporting element of a removable component is manufactured to overlap at least partly with the volume of the other of the removable component and the cavity wall, such that a tight fit is created between the cavity and the removable component.

In some embodiments the volume of the overlap is adapted to be controlled by an operator.

In some embodiments the method comprises providing that the model comprises a side ejection hole through which the removable component in the physical model can be contacted and ejected from its cavity.

The hole may be arranged in the gingival part of the model.

It may be an advantage that when providing an ejection hole in the side on the model, then this hole is accessible from the side, which may be an advantage when e.g. mounting the model on an articulator, where the side of the model can be accessed as opposed to the bottom of the model which is attached to the articulator. Therefore it may be an advantage to arrange the ejection hole on the side of the model instead of in the bottom of the model. However, a hole, e.g. an ejection hole, may alternatively and/or additionally be arranged in the bottom of the model.

In some embodiments, the method comprises providing that the removable component comprises a hole adapted to be arranged in continuation of the side ejection hole in the model, when the removable component is arranged in the cavity of the model.

It may be an advantage that when providing a hole in the side of the model and a hole in the removable component, then when the two holes are aligned, i.e. arranged in continuation of each other, or arranged end to end, then the removable component is arranged correctly relative to the model.

Whether the hole in the removable component and the hole the in model are aligned can be checked by means of visual inspection or by using a tool adapted to fit into the holes. Thus when the tool can move trouble-free through the hole in the model and into the hole in the removable component, then the alignment of the removable component in the model will be correct. In some embodiments the side ejections hole is arranged such that the tool can move the entire way through both the model and the removable component, thus the tool is inserted on one side of the model and can pass through the model to the other side of the model. Thus in some embodiments, the side ejection hole is arranged such that a tool can pass through a section of the model comprising both the removable component and the gingival part of the model surrounding the cavity in which the removable component is arranged, such that the tool can be inserted on one side of the section and can pass through the section to a side of the section arranged opposite to the removable component.

In some embodiments the method comprises arranging the hole in the model as a through hole passing from the surface of model to the cavity for the removable component, and arranging the hole in the removable component as a blind hole.

The through hole may be passing from the gingival part of the model. The hole in the removable component may be arranged as a blind hole in a position corresponding to the root of the tooth.

In some embodiments the method comprises arranging the hole in the model as a through hole passing from the surface of model to the cavity for the removable component, and arranging the hole in the removable component as a through hole.

The through hole may be passing from the gingival part of the model. The hole in the removable component may be arranged as a through hole in a position corresponding to the root of the tooth.

Thus the hole in the removable component may be a through hole passing the entire way through the removable component to the other side of the cavity. In this case the hole in the model may then pass through the entire model, i.e. passing from the surface of the model to one end of the cavity inside the model, and from the other end of the cavity through the model to the other surface of the model.

It may be an advantage to have a side ejection hole which is a through hole in both the model and the removable component, since then the positioning of the removable component in the model can be checked by visual inspection, which may be facilitated when there is a free passage through the entire model and removable component.

Furthermore, it may be an advantage for the manufacturing of the model and the removable component to produce the side ejection holes a through holes. For example, the model and removable component can be manufactured by means of jet printing, and for example a soft support material may be arranged in the model and the removable component at places where there should be no material in the final version. When the manufacturing of the model or the removable component has been completed, the support material will be removed, e.g. washed away, melted away or digged away. In this case it may be easier to remove all the support material from a hole if the hole is a through hole instead of a blind hole.

In some embodiments the method comprises arranging the removable component in the gingival part of the model such that the removable component is adapted to be inserted in and removed from the gingival part of the model without conflicting with or being blocked by the neighbor teeth in the model.

In some embodiments the method comprises arranging the removable component in the model such that the insertion direction of the removable component corresponds to the insertion direction of the real, anatomical tooth in the set of teeth.

In some embodiments the method comprises arranging the removable component in the gingival part of the model such that the insertion direction of the removable component is so skew that the removable component is adapted to be inserted in and removed from the gingival part of the model without conflicting or being blocked by the neighbor teeth in the model.

In some embodiments the method comprises providing that the model comprises a stop surface functioning as a stop for the removable component when arranged in the cavity, such that the removable component is hindered from being pushed further into the gingival part of the model than the correct anatomical height of the removable component corresponds to.

In some embodiments the stop surface is plane and horizontal.

The stop surface may be plane and horizontal relative to the rest of the model, and/or relative to the insertion direction of the removable component etc.

It may be an advantage that the stop surface is plane and horizontal since this may provide an optimal positioning and support of the removable component in the model.

In the context of the present invention, the phrase "horizontal" may refer to a plane which is substantially parallel to the occlusion plane of the patient's dentition.

In some embodiments the method comprises that when the model is 3D printed, at least part of the stop surface is horizontal with respect to the remainder of the model.

Thus the overall form of the stop surface may be sloping, slanting or inclined, but each single printing layer should be horizontal so the sloping surface will be made up of several small horizontal parts. This provides a very good set fit.

If the model is milled instead of 3D printed, then the stop surface may not be horizontal, but can be in any direction.

In some embodiments the method comprises that the stop surface is arranged in a printing layer which is also present in the remainder of the model.

It may be an advantage because the stop surface is then level with the bottom part of the removable component, whereby the removable component can be pushed down exactly to the right layer in the model, whereby the position of the removable component in the model is anatomically correct with respect to the height of the removable component in the physical model.

Thus the stop layer is at a height h which is h=n×printing layer thickness.

In some embodiments the method comprises providing that the removable component has a top part, which is visible, when the removable component is arranged in its corresponding cavity in the model, and a bottom part, which is hidden by the gingival part of the model and therefore not invisible, when the removable component is arranged in its corresponding cavity in the model.

In some embodiments the method comprises providing that at least the bottom part of the removable component is substantially cylindrical.

In some embodiments the method comprises providing that at least the bottom part of the removable component is substantially rectangular.

An advantage of this embodiment is that when the bottom part of the removable component is rectangular, the removable component cannot rotate in the cavity, and its positioning in the model is therefore well fixed.

In some embodiments the method comprises that the cross section area of the removable component is constant along the part of the removable component, which is adapted to be covered by the gingival part of the model, when the removable component is inserted in its cavity.

In some embodiments the method comprises that the cross section area of the removable component is constant along the part of the removable component, which is arranged at said interface, when the removable component is inserted in its cavity. An advantage of this is that when the removable component has a constant thickness in the model, then the removable component may have a stable fit, for example without using any pins.

The part of the removable component which is covered by the gingival part of the model is not visible, when the removable component is arranged in the model, and when the model is made in a non-transparent material. However, if the model is made in a transparent material, then the part of the removable component which is in the cavity of the model, may still be visible.

In some embodiments the method comprises that the shape of the cross section is constant along the part of the removable component, which is adapted to be covered by the gingival part of the model, when the removable component is inserted in its cavity.

In some embodiments, the method comprises that the shape of the cross section is constant along the part of the removable component, which is arranged at said interface, when the removable component is inserted in its cavity.

In some embodiments the method comprises providing that one or more adjacent teeth of the removable component in the model are adapted to be removably inserted in the model.

An advantage is that when the adjacent or neighbor teeth can be removed from the model, then it may be easier for the dental technician to build up the model of a restoration, since then there is free space around the removable component, e.g. on all or some of the sides.

In some embodiments the method comprises providing that the removable component comprises an anatomical layer, a margin line layer, a connection layer and a base layer.

In some embodiments the removable component comprises a ditch layer arranged between the margin line layer and the connection layer for providing workspace.

An advantage of this embodiment is that the ditch layer provides working space on the removable component for the dental technician, such that the dental technician have space enough to work with for example a dental drill etc.

In some embodiments the removable component comprises a pin.

An advantage of this embodiment is that a pin may provide a better fit of the removable component in the model.

In some embodiments the method comprises providing an identification tag on at least one removable component.

In some embodiments the method comprises providing an identification tag on each removable component. This identification tag may be provided when manufacturing the removable component and the model.

It may be an advantage because when providing an identification (ID) tag then it is easy to identify the removable components, when for example a large batch of removable components are manufactured together. The ID tag may be printed a suitable place in the removable component, may be attached to the model and may be detachable etc.

The identification tag may be provided on the virtual model and/or the physical model.

In some embodiments the method comprises providing a identification number on each removable component and providing the corresponding identification number at the corresponding cavity in the model for each removable component.

It may be an advantage because if there are several removable components in a model, then it may be complicated to find out or see where each removable component should be arranged in the model. When providing the identification numbers then it is easy and fast to arrange the removable components in their correct cavities in the model.

In some embodiments the method comprises providing visual guidelines on the removable component and the gingival part of the model for arranging the removable component correct relative to the gingival part of the model.

The visual guidelines may be printed, embossed etc., and may be grooves or elevations.

In some embodiments the method comprises manufacturing the model to be hollow.

It may be an advantage because then less material is used, and the smaller amount of material that is used, the smaller will the degree of distortion of the model be after manufacturing There may also be an economic advantage of providing a hollow model, because using less material makes the manufacturing process less costly and possibly also faster.

In some embodiments the method comprises providing the model with connector pins. The connector pins may be configured such that they connect the model to e.g. an articulator.

It may be an advantage because if both a model of the upper jaw and a model of the lower jaw are manufactured, then the two models can be connected by the connector pins such that the occlusion of the patient can be tested, e.g. by arranging the upper and the lower model in an articulator.

In some embodiments the method comprises providing the model with an interface adapted for matching a specific articulator in which the occlusion of the patient is tested.

In some embodiments the method comprises manufacturing an articulator plate matching the interface of the model.

The present disclosure relates to different aspects including the method described above and in the following, and corresponding methods, devices, systems, uses and/or product means, each yielding one or more of the benefits and advantages described in connection with the first mentioned aspect, and each having one or more embodiments corresponding to the embodiments described in connection with the first mentioned aspect and/or disclosed in the appended claims.

In particular, it is disclosed herein is a computer-implemented method of generating a virtual model of a set of teeth for manufacturing a physical model of the set of teeth, where the model comprises one or more teeth preparations, where the method comprises:

generating a virtual model of the set of teeth, where the virtual model is based on a virtual representation of the set of teeth;

providing that each of the teeth preparations is configured to be arranged as part of a removable component in the model, where each removable component is adapted to fit into a corresponding cavity in the gingival part of the model;

providing means for supporting and positioning each of the removable components in their corresponding cavity in the model.

providing a pin at the base of each removable component, where the pin is shaped so that it resembles the shape of the removable component.

In particular, disclosed herein is a computer-implemented method of generating a virtual model of a set of teeth for manufacturing a physical model of the set of teeth, where the method comprises:

generating a virtual model of the set of teeth, where the virtual model is based on a virtual representation of the set of teeth;

providing that at least one tooth is configured to be arranged as part of a removable component in the model, where the removable component is adapted to fit into a corresponding cavity in the gingival part of the model;

providing means for supporting and positioning each of the removable components in its corresponding cavity in the model.

providing a pin at the base of the removable component.

The cross sectional shape of the pin may resemble the cross sectional shape of the base of the removable component.

In particular, disclosed herein is a system for generating a virtual model of a set of teeth for manufacturing a physical model of the set of teeth, where the model comprises one or more teeth preparations, where the system comprises:

means for generating a virtual model of the set of teeth, where the virtual model is based on a virtual representation of the set of teeth;

means for providing that each of the teeth preparations is configured to be arranged as a removable component in the model, where each removable component is adapted to fit into a corresponding cavity in the gingival part of the model;

means for providing means for supporting and positioning each of the removable components in their corresponding cavities in the model.

The system further comprises:

means for configuring the means for supporting and positioning such that the area of contact between each removable component and its corresponding cavity is smaller than the area in which there is no contact between the removable component and the cavity.

Disclosed is a computer-implemented method of generating a virtual model of a set of teeth for manufacturing a physical model of the set of teeth, the method comprising:

providing a virtual representation of a set of teeth;
generating a virtual model of the set of teeth from said virtual representation, said virtual model comprising a gingival part and at least one tooth, said generating comprising:
a: configuring said tooth to be part of a removable component in the model;
b: defining a cavity in said gingival part, said cavity comprising a cavity wall; and
c: defining means for supporting and positioning capable of supporting and positioning the removable component in the cavity in a physical model manufactured from the virtual model;
wherein the removable component and the cavity are configured so that the removable component fits into the cavity such that an interface between the removable component and the cavity wall is defined and such that the removable component and the cavity provide a gap at said interface;
wherein the means for supporting and positioning are generated on one of said removable component and said cavity wall such that the means for supporting and positioning extends across said gap between said removable component and said cavity wall; and
wherein the area of contact between the removable component and the cavity wall at said interface is controlled by the shape of the adjoining surfaces of the means for supporting and positioning and the other of the removable component or the cavity wall.

In some embodiments, a) is performed before b), such that the method comprises configuring said tooth to be part of a removable component in the model before the cavity.

In some embodiments, b) is performed before a), such that the method comprises defining said cavity before the said tooth is configured to be part of a removable component in the model.

In some embodiments, said means for supporting and positioning, said removable component and the corresponding cavity are formed in one step.

Disclosed is a computer-implemented method of generating a virtual model of a set of teeth for manufacturing a physical model of the set of teeth, the method comprising:
providing a virtual model of the set of teeth, the model comprising a gingival part and a tooth configured to be part of a removable component in the model;
generating a cavity in said gingival part, said cavity comprising a cavity wall, into which cavity said removable component fits such that an interface between the removable component and the cavity wall is defined, where the removable component and the cavity are configured to provide a gap at said interface; and
providing means for supporting and positioning on the removable component and/or on the cavity wall such that in a physical model manufactured from the virtual model, the means for supporting and positioning extends across said gap between said removable component and said cavity wall such that the means for supporting and positioning support and position the removable component in the cavity;
wherein the area of contact between the removable component and the cavity wall at said interface is controlled by the shape of the adjoining surfaces of the means for supporting and positioning and the cavity wall and/or the removable component.

Disclosed is a computer-implemented method of generating a virtual model of a set of teeth for manufacturing a physical model of the set of teeth, where the method comprises:
providing a virtual model of the set of teeth;
providing that at least one tooth is configured to be arranged as a part of removable component in the model, where the removable component is adapted to fit into a corresponding cavity in the gingival part of the model such that an interface between the removable component and a cavity wall is defined;
providing means for supporting and positioning the removable components in the cavity in the model; and
configuring the means for supporting and positioning such that the area of contact between the removable component and the cavity wall is smaller than the area of said interface.

Disclosed is a computer-implemented method of controlling the area of contact between a gingival part of a model of a set of teeth and a removable component in the model, said removable component comprising a tooth, wherein the method comprises:
providing a virtual model of the set of teeth, the model comprising a gingival part and a tooth configured to be part of a removable component in the model, where said gingival part comprises a cavity comprising a cavity wall, into which cavity said removable component fits such that an interface between the removable component and the cavity wall is defined, where the removable component and the cavity are configured to provide a gap at said interface; and
providing means for supporting and positioning on one of said removable component and said cavity wall such that in a physical model manufactured from the virtual model, the means for supporting and positioning extends across said gap between said removable component and said cavity wall such that the means for supporting and positioning support and position the removable component in the cavity;
wherein the area of contact between the removable component and the cavity wall at said interface is controlled by the shape of the adjoining surfaces of the means for supporting and positioning and the other of the removable component and the cavity wall.

Disclosed is also a computer program product comprising program code means for causing a data processing system to perform the method, when said program code means are executed on the data processing system, and a computer program product comprising a computer-readable medium having stored there on the program code means.

According to another aspect, disclosed is also an ejection tool for ejecting a removable component arranged in a physical model of a set of teeth.

In some embodiments the ejection tool comprises an elongated component which is adapted to fit into a through hole in the gingival part of the model.

In some embodiments the ejection tool is adapted to fit into a blind hole and/or a through hole in the removable component.

BRIEF DESCRIPTION OF THE DRAWINGS

The above and/or additional objects, features and advantages of the present disclosure, will be further elucidated by the following illustrative and non-limiting detailed description of embodiments of the present invention, with reference to the appended drawings, wherein:

FIG. 9-11 shows an example of a removable component and model with a side ejection hole.

FIG. 14 shows an example of a cavity of a model and a removable component with non-straight sides.

FIG. 15 shows an example of a cavity of a model and a removable component with non-straight sides.

DETAILED DESCRIPTION OF PREFERRED EMBODIMENTS

In the following description, reference is made to the accompanying figures, which show by way of illustration how the invention may be practiced.

Figure 1:
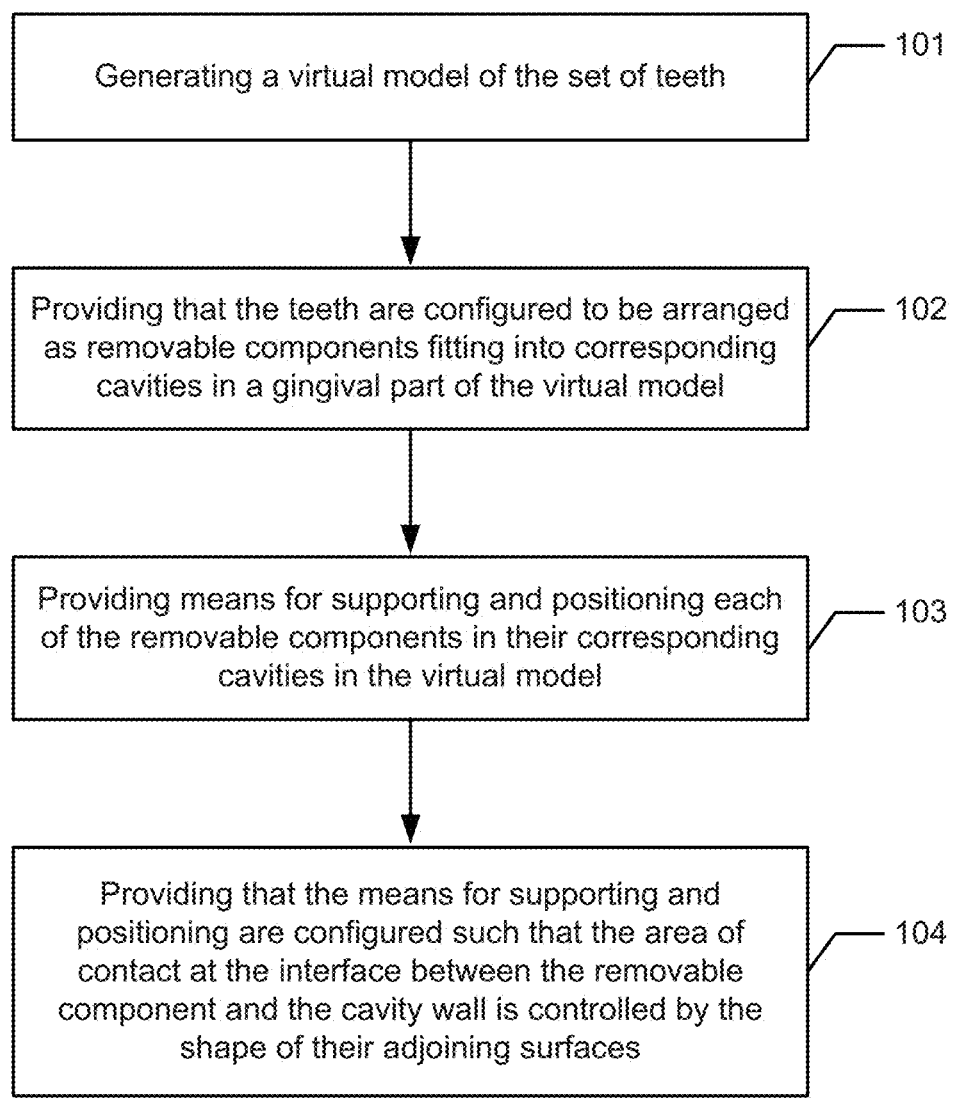
FIG. 1 shows an example of a flow chart of the method.

FIG. 1 shows an example of a flow chart of one embodiment of the method.

In step 101 a virtual model of a set of teeth is generated, and the virtual model is based on a virtual representation of the set of teeth. The virtual representation may be provided by scanning an impression of the set of teeth or scanning the set of teeth directly in the mouth of the patient using an intraoral scanner. The virtual model may comprise one or more teeth. The virtual model may have been generated previously and the invention is not limited to methods including the generation of the virtual model.

In step 102 each of the teeth are provided to be configured to be arranged as a removable component in the model, and each removable component is adapted to fit into a corresponding cavity in the gingival part of the model.

In step 103 means for supporting and positioning each of the removable components in their corresponding cavities in the model are provided.

In step 104 the means for supporting and positioning are configured such that the area of contact at the interface between the removable component and the cavity wall is controlled by the shape of the adjoining surfaces of the means for supporting and positioning and the removable component or the cavity wall.

The invention is not limited to a method and systems wherein these steps are performed in the abovementioned order. For instance, step 103 may be performed before step 102, or the steps may be performed simultaneously.

Figure 2:
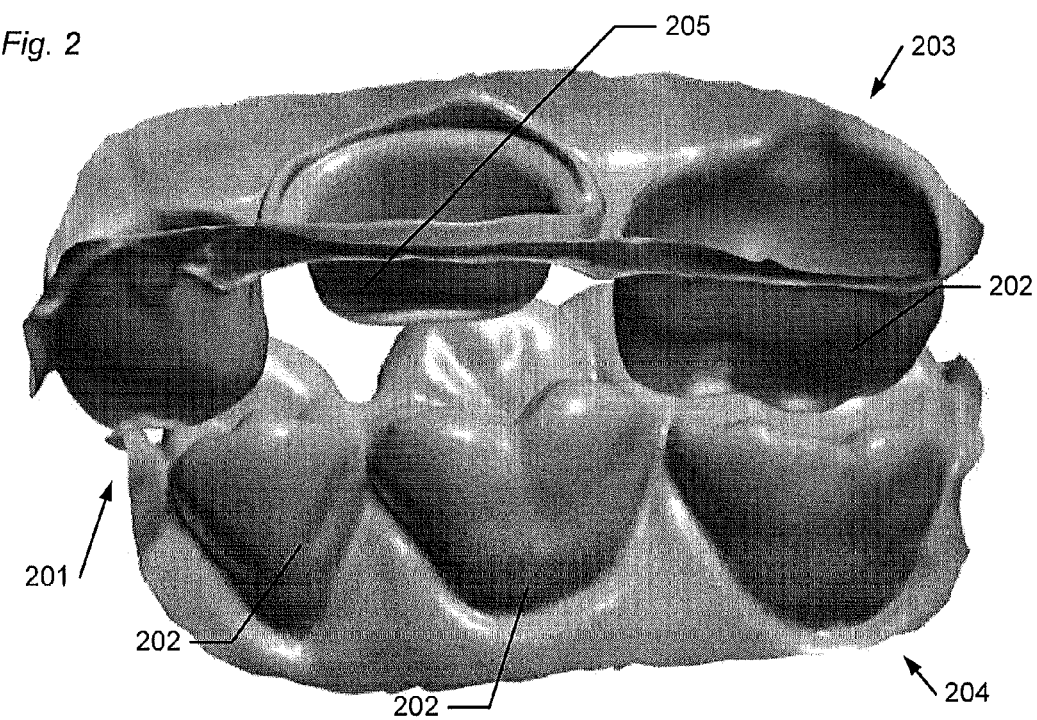
FIG. 2 shows an example of a virtual model of a set of teeth seen from the side.

FIG. 2 shows an example of a virtual model of a set of teeth seen from the side.

The virtual model 201 shows a number of teeth 202 in both the upper 203 and lower 204 jaw. A tooth preparation 205 is shown in the upper jaw 203.

The virtual model 201 is hollow, thus only forming a shell indicating the surface contour of the teeth. The virtual model 201 may be provided by e.g. scanning an impression.

Figure 3:
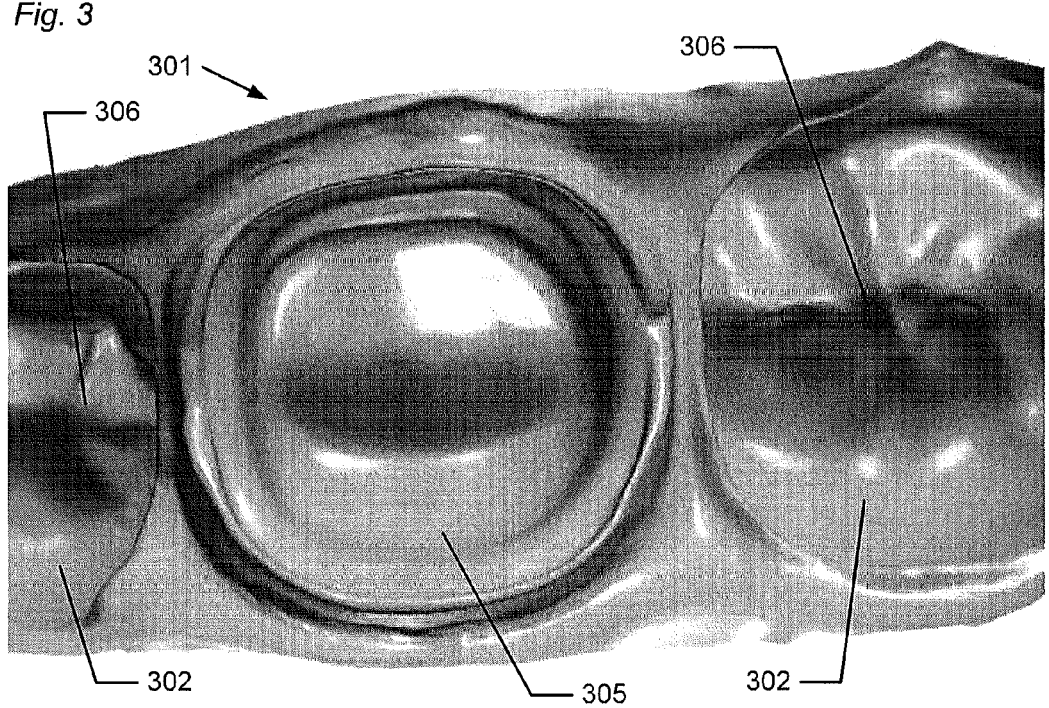
FIG. 3 shows an example of a virtual model of a set of teeth seen from above.

FIG. 3 shows an example of a virtual model of a set of teeth seen from above. The virtual model 301 shows a number of teeth 302 and a tooth preparation 305 seen from above. The cusps 306 of the teeth 302 can be seen, whereas there are no cusps on the prepared tooth 305, because the cusps here has been removed when preparing the teeth for a dental restoration, such as e.g. a crown or a bridge.

FIG. 4 shows an example where a tooth preparation is a removable component in the model.

Figure 4A:
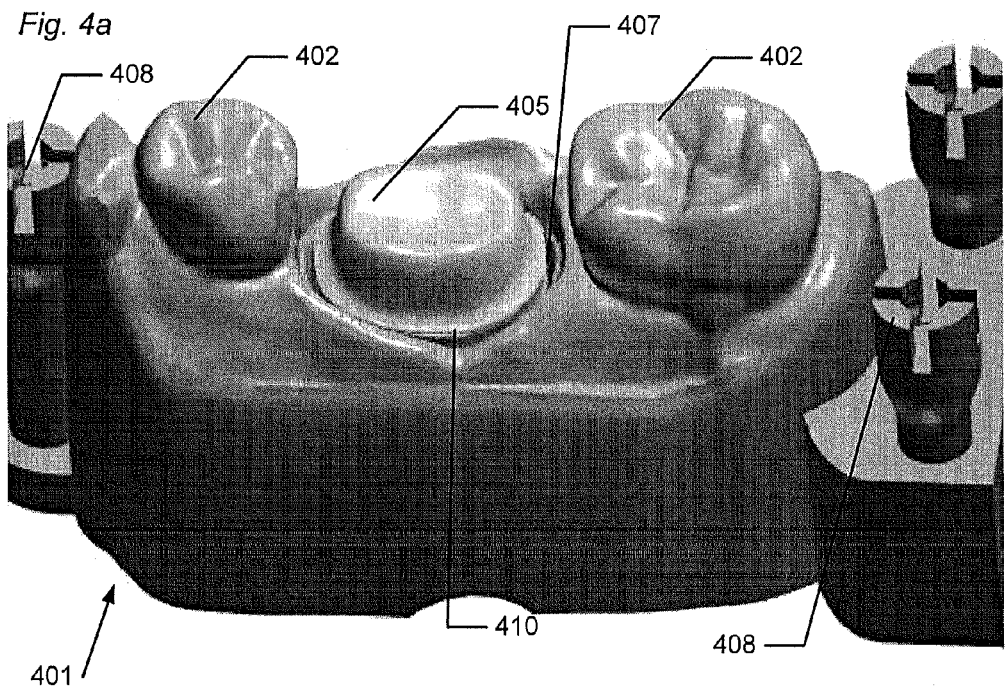
FIG. 4 shows an example where a tooth is a removable component in the model.

In FIG. 4a) a model 401 of a set of teeth is shown, and the set of teeth comprises a couple of teeth 402 and a tooth preparation 405. The tooth preparation 405 is arranged as a removable component in its corresponding cavity 407 in the model 401.

Some of the part of the model 401 corresponding to the gingiva may have been removed, such that it is easier for a user to take the removable component 405 out of the model 401.

The margin line 410 for the removable component 405 may have been automatically defined based on the centre of mass of the removable component 405.

Figure 4B:
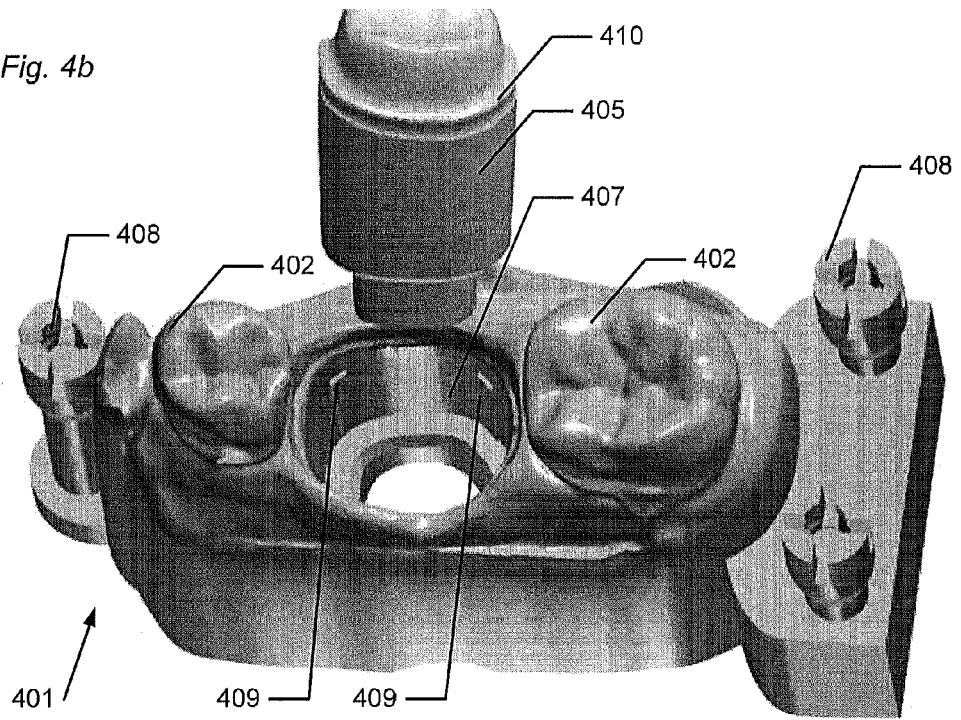

In FIG. 4b) a tooth preparation 405 is shown as a removable component lifted up from the cavity 407 and thus the removable component is arranged outside its corresponding cavity 407 in the model 401.

Supporting elements 409 supporting and positioning the removable component 405 in the cavity 407 is seen, when the removable component 405 is lifted away from the cavity 407. In this example the supporting elements are shown as friction points with a shape of cut-off pyramids or rectangular frusta.

In both FIG. 4a) and FIG. 4b) connector pins 408 are seen on the model 401. By means of connector pins 408 a lower jaw and an upper jaw model of a set of teeth can be connected together in an anatomically correct way.

FIG. 5 shows in a perspective view examples of supporting elements.

Figure 5A:
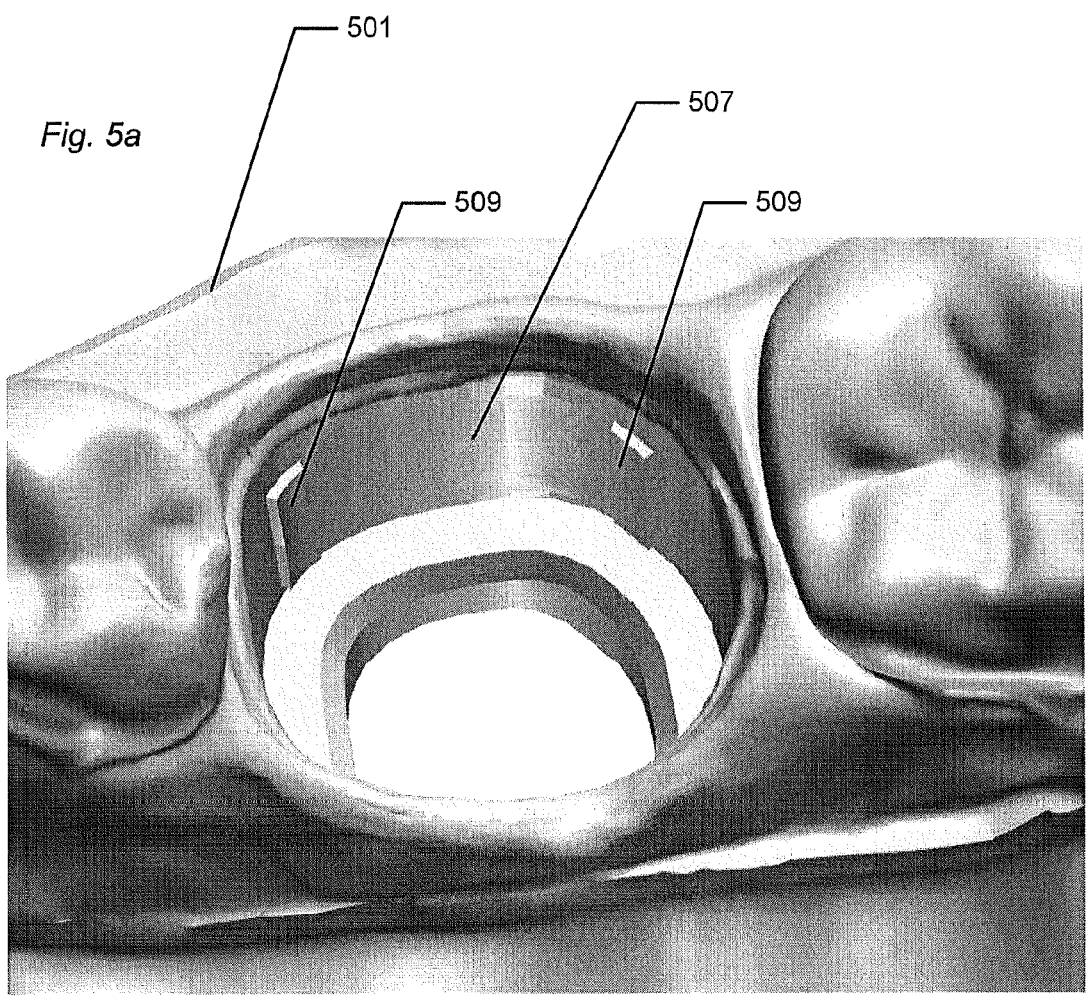
FIG. 5 shows in a perspective view examples of supporting elements

FIGS. 5a), 5b) and 5c) all show a cavity 507 with supporting elements 509 in the form of friction points shaped as cut-off pyramids or rectangular frusta. The cut-off pyramids or rectangular frusta are arranged with the broadest part arranged at the surface of the cavity and the narrowest part pointing towards the position, where the removable component is configured to be arranged.

In FIG. 5a) two friction points 509 are seen, in FIG. 5b) four friction points are seen, and in FIG. 5c) three friction points are seen.

The friction points are shaped so that they follow the surfaces of the removable component and of the cavity 507 at the interface, and there is a constant distance from the part of the friction point pointing towards the position of the removable component to the surface of the cavity, i.e. the friction points have a constant height.

In FIG. 5b) four friction points are arranged in positions corresponding to the four corners of the removable component and of the cavity.

The friction points are arranged such that the friction points are substantially opposing each other two and two or in pairs.

Some of the part of the model 501 corresponding to the gingiva may have been removed, such that it is easier for a user to take the removable component out of the model 501.

Figure 6:
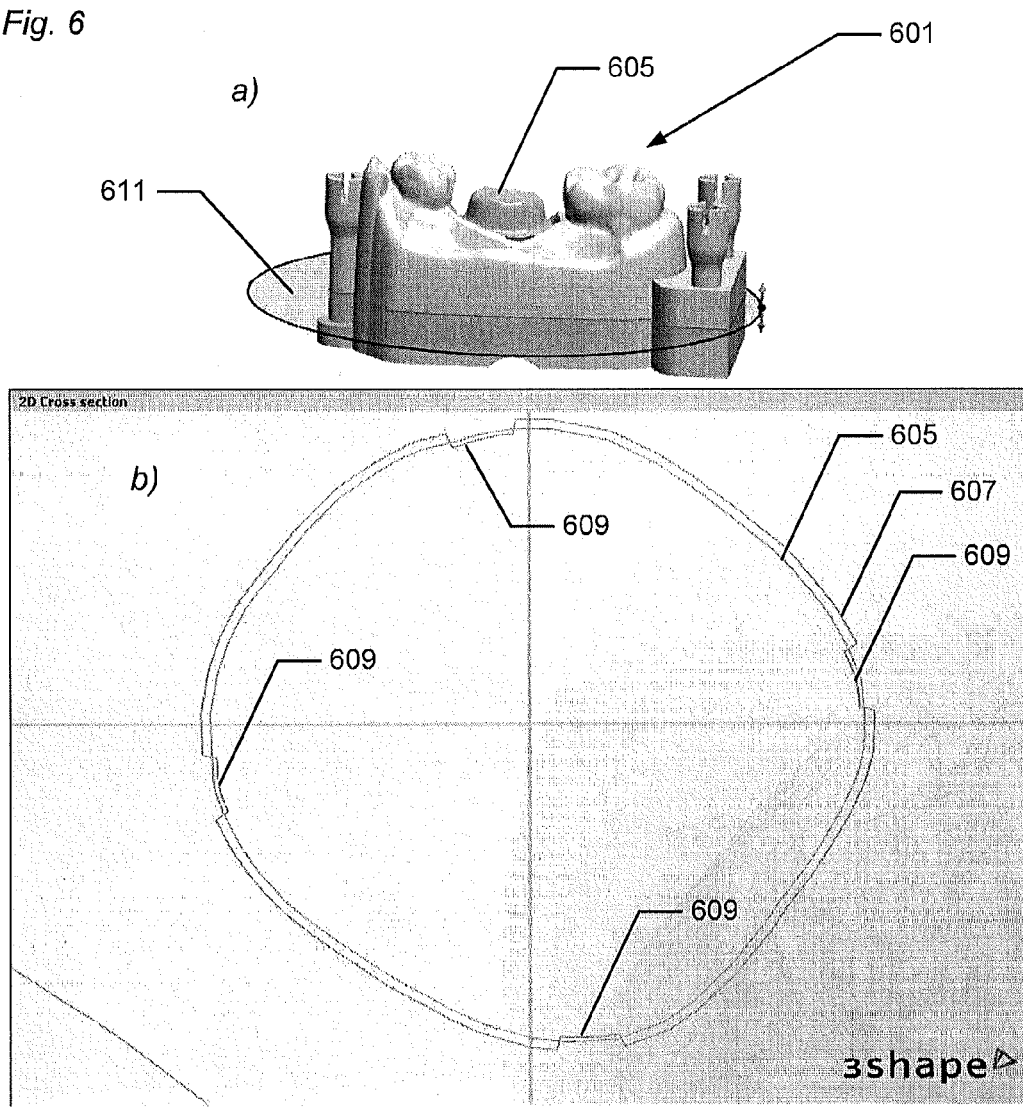
FIG. 6 shows an example of an intersection plane of the model.

FIG. 6 shows an example of an intersection plane of the model.

FIG. 6*a*) shows the model 601 with an intersection plane 611. The model 601 comprises the removable component 605.

FIG. 6*b*) shows the cross section of the removable component 605 and the cavity 607 at the intersection plane seen in FIG. 6*a*).

Supporting elements 609 are shown as friction points in the cross section view in FIG. 6*b*). The contour of the cavity 607 and the contour of the removable component 605 are parallel, thus there is a constant distance between the contours, except at the friction points 609, where the distance is another constant distance.

In FIG. 6*b*) of the cross section is seen that at the supporting elements 609, the contour of the supporting elements 609 or friction points in the cavity overlap the contour of the removable component 605 a little bit, and this will provide that the removable component 605 is firmly arranged in the cavity 607. Thus the friction is created due to that the removable component and the cut-off pyramids overlap a small distance, e.g. a few millimeters. The overlap may be one tenth, one hundredth or the like of a millimeter.

Figure 7:
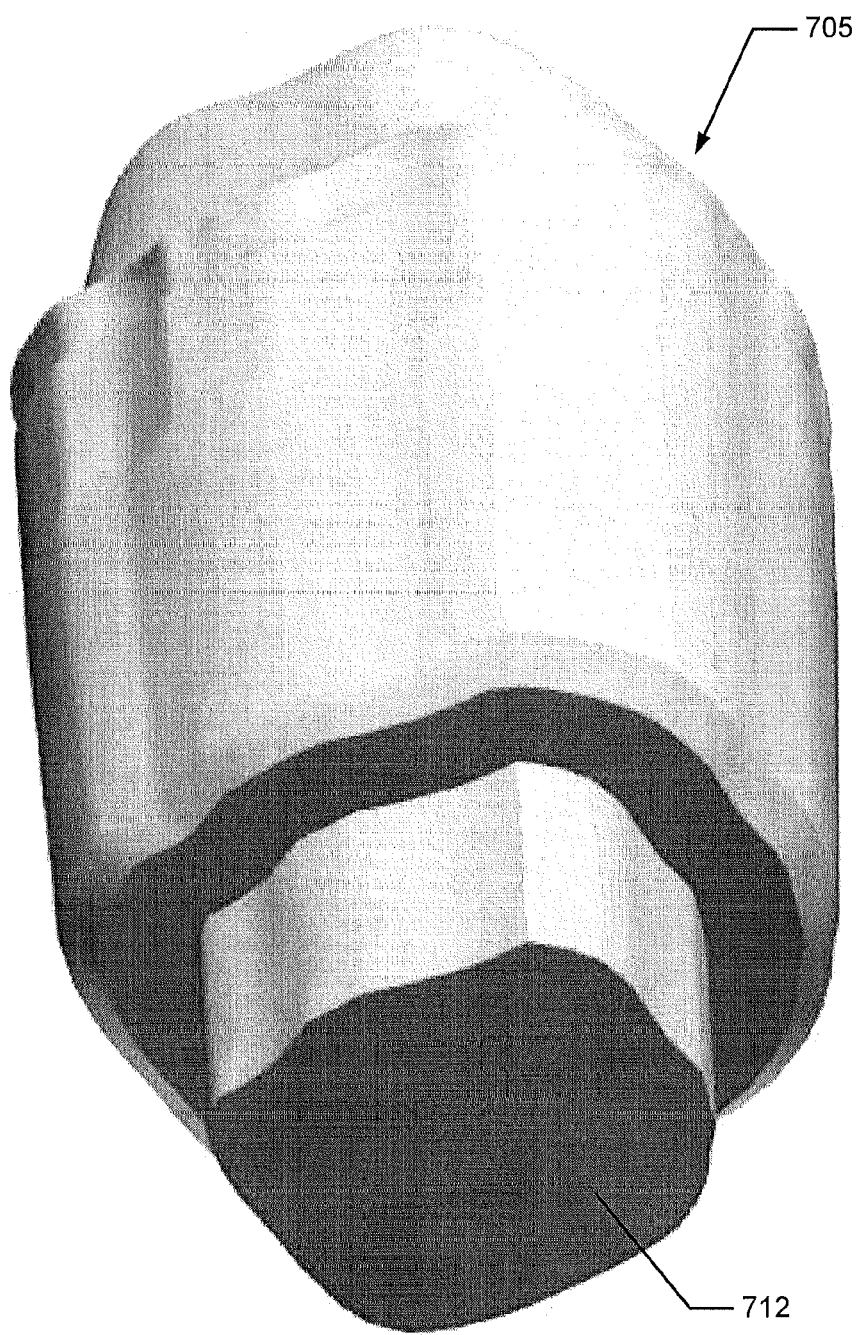
FIG. 7 shows an example of a removable component with a pin having a shape corresponding to the shape of the base of the removable component.

FIG. 7 shows an example of a removable component with a pin having a shape corresponding to the shape of the base of the removable component, i.e. the pin is shaped so that its cross sectional shape resembles the cross sectional shape of the base of the removable component.

The removable component 705 comprises a pin 712 which has a shape resembling the shape or contour of the removable component 705. The pin may be wider or narrower, longer or shorter than shown in this example. A large pin may provide good support for the removable component 705 in a physical model of a set of teeth.

FIG. 8 shows an example of a side view of a removable component in a model with a side ejection hole and a bottom ejection hole.

Figure 8A:
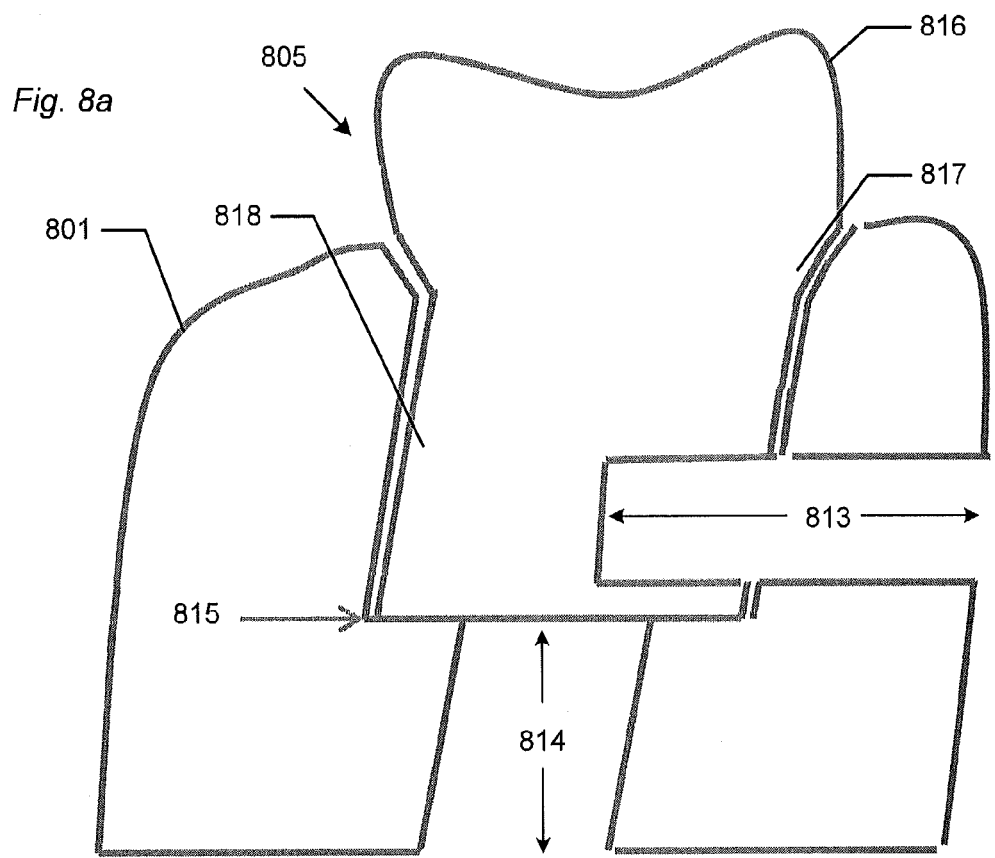
FIG. 8 shows an example of a side view of a removable component in a model with a side ejection hole and a bottom ejection hole.

FIG. 8*a*) shows a removable component 805 arranged in a gingival part of the model 801. The model 801 with the removable component 805 comprises a side ejection hole 813. The side ejection hole 813 is a through hole in the side of the model 801, and a blind hole in the side of the removable component 805. The model 801 also comprises a bottom ejection hole 814, which is a through hole in the bottom of the model 801. When the removable component 805 is arranged in the model 801 it rests on the stop surface 815 of the model 801, and the bottom of the removable component 805 forms the end of or closes the bottom ejection hole 814. The stop surface may be plane and horizontal for providing an optimal positioning and support of the removable component in the model.

The side election hole 813 and the bottom ejection hole can be used for ejecting the removable component 805 from the gingival part of the model 801.

The removable component comprises an anatomical part 816, which is the top of the removable component, and a bottom, standard part 818 which is the part arranged in the cavity 807 of the model 801, and a connection area 817, which is the part between the anatomical part 816 and the bottom standard part 818.

Alternatively and/or additionally, the bottom standard part 818 is not arranged in a cavity 807 of the model 801, but may be arranged on a model 801 having no cavities.

Figure 8B:
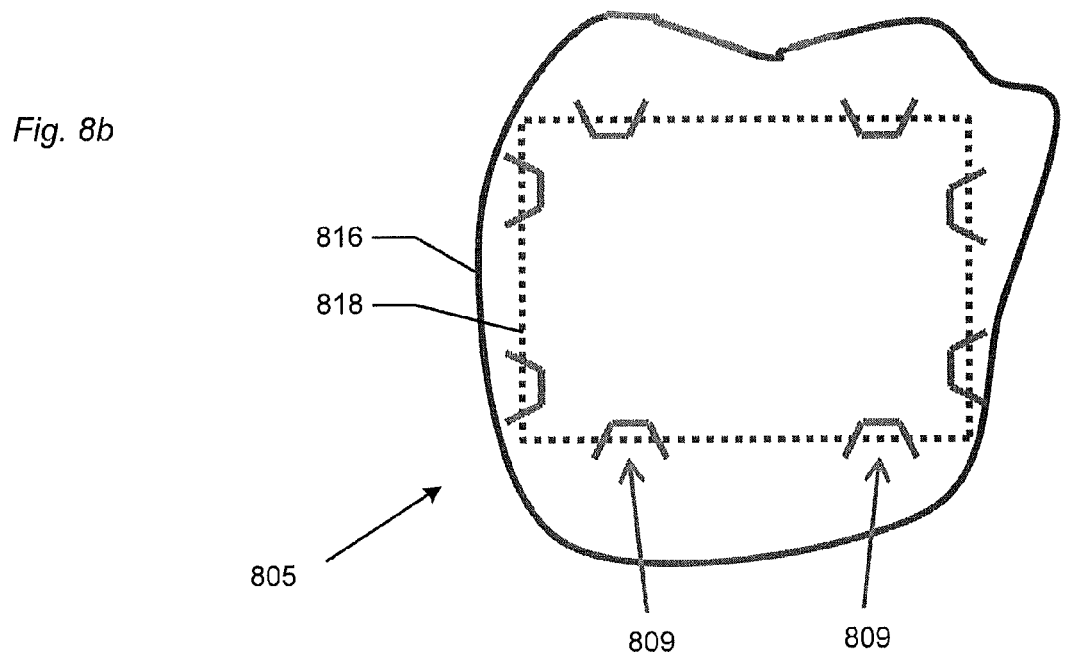

FIG. 8*b*) shows an example of a top view of a removable component 805.

The line 816 shows the anatomical part 816 of the removable component, and the line 818 shows the bottom, standard part 818 of the removable component, as seen in FIG. 8*a*). The cut-off triangles or crushing pyramids show the friction points 809 on the model 801. The friction points 809, in e.g. the cavity of the model 801, have the function to facilitate support and positioning of the removable component 805 in the model 801.

FIG. 9 shows an example of a removable component and model with a side ejection hole which is a through hole.

Figure 9A:
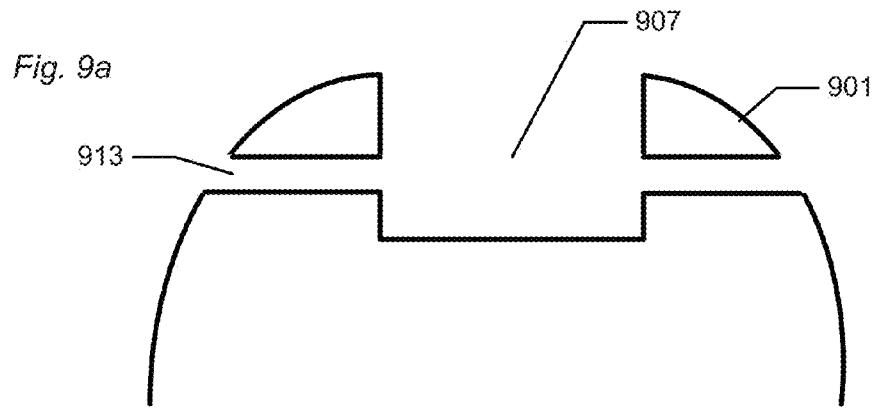

FIG. 9*a*) shows a side view of a part of a model 901 with a side ejection hole 913 being a through hole. The side ejection hole 913 is a through hole from the outside surface of the model 901 to the cavity part 907 of the model and again from the other end of the cavity part 907 to the other surface of the model 901.

Figures 9B, 9C:
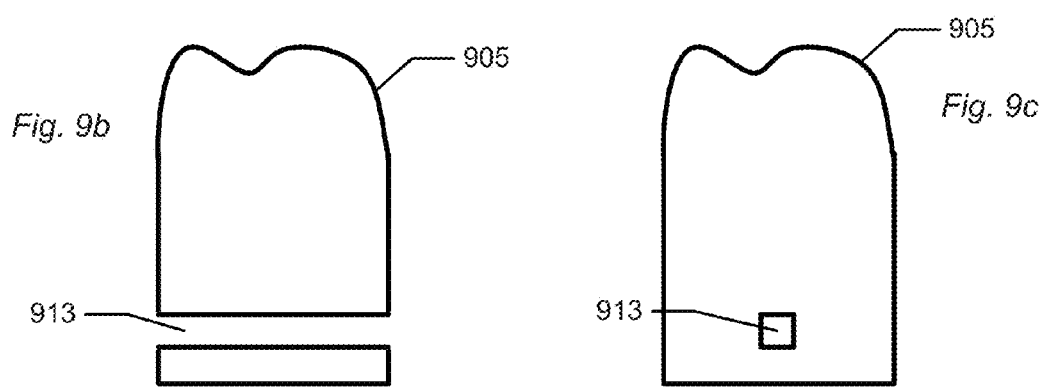

FIG. 9*b*) shows a side view of a removable component 905 fitting into the cavity 907 of the model 901. The side ejection hole 913 is a through hole in the bottom part of the removable component 905. FIG. 9*c*) shows a side view of the removable component 905, where the removable component has been rotated 90 degrees relative to the view in FIG. 9*b*), so that the side ejection hole 913 is seen from the front.

Figure 9D:
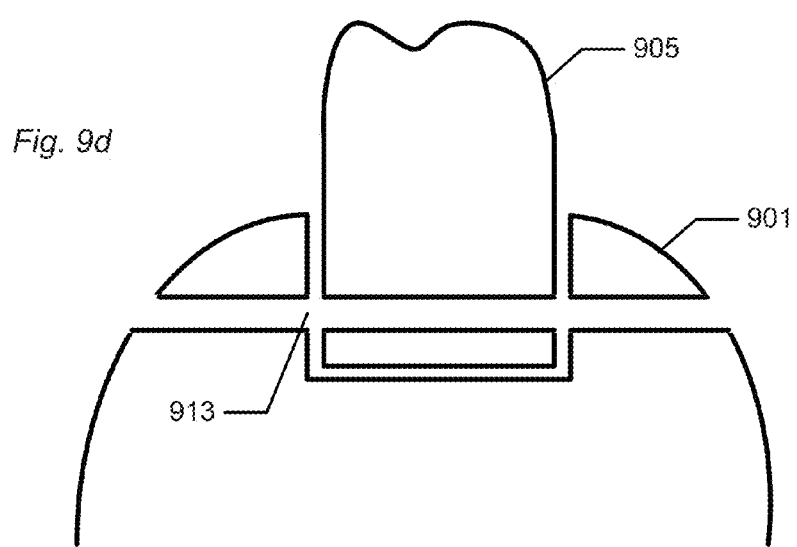

FIG. 9*d*) shows a side view of the model 901 with the removable component 905, where the removable component 905 is arranged in the cavity 907 of the model 901. It is seen that the side ejection hole 913 in the removable component 905 and in the model 901 are arranged exactly on line such that the part of the side ejection hole 913 in the removable component 905 and the part of the side ejection hole in the model 901 are arranged exactly end to end.

FIG. 10 shows an example of a model with a removable component with a side ejection hole 1013, where the hole in the removable component 1005 is a through hole passing along the entire width of the removable component 1005. The side ejection hole 1013 only passes through one side of the model 1001, but not through the other side of the model.

The cavity 1007 of the model 1001, see FIG. 10*a*), and the bottom, standard part 1018 of the removable component 1005, see FIG. 10*b*), have straight sides that are arranged with a slope. Thus the sides do not form straight angles.

FIG. 10*c*) shows the model 1001 with the removable component 1005.

FIG. 11 shows an example of a model with a removable component with a side ejection hole 1113, where the hole in the removable component 1105 is a blind hole.

FIG. 11 shows that the side ejection hole 1113 of the model 1101 is straight, but that the blind hole 1113 of the removable component 1105 has a sloping side.

Furthermore, the model 1101 comprises a bottom ejection hole 1114.

Figure 12:
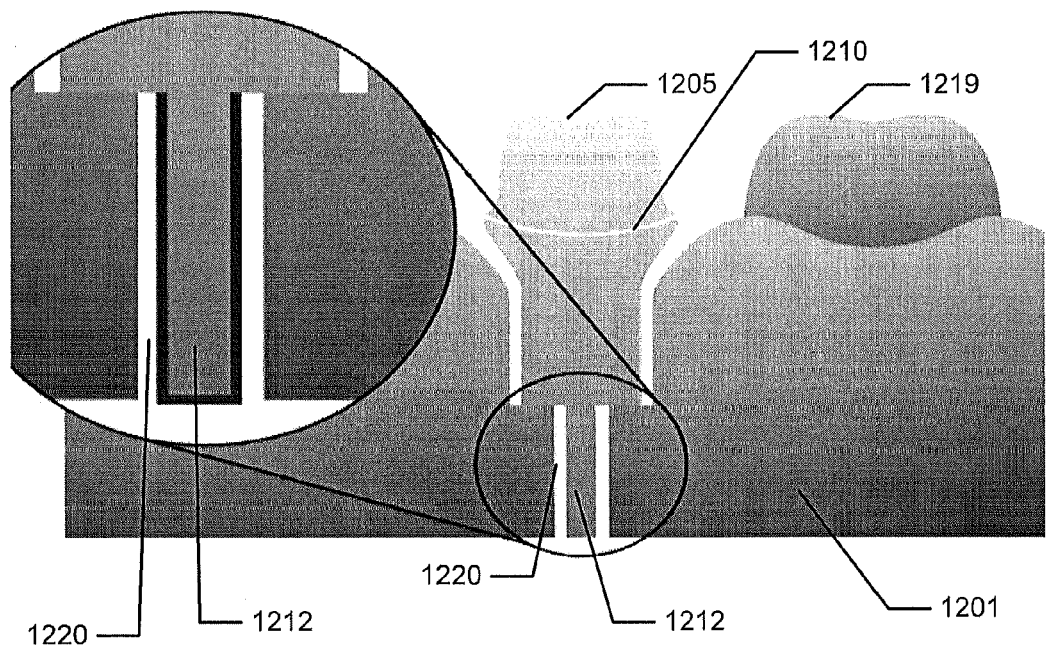
FIG. 12 shows an example of a removable component with a pin in a model.

FIG. 12 shows an example of a removable component with a pin in a model. The figure shows that the removable component 1205 is arranged in a model 1201. The model 1201 does not comprise a cavity, so the removable component 1205 is just arranged next to the adjacent or neighbour teeth 1219 in the free space in the model 1201. The removable component 1205 comprises a thin, elongated pin 1212 which fits into a hole 1220 in the model 1201, see also the blow up showing an enlargement of the pin 1212 and the hole 1220.

The margin line 1210 of the removable component 1205 is also marked.

Figure 13:
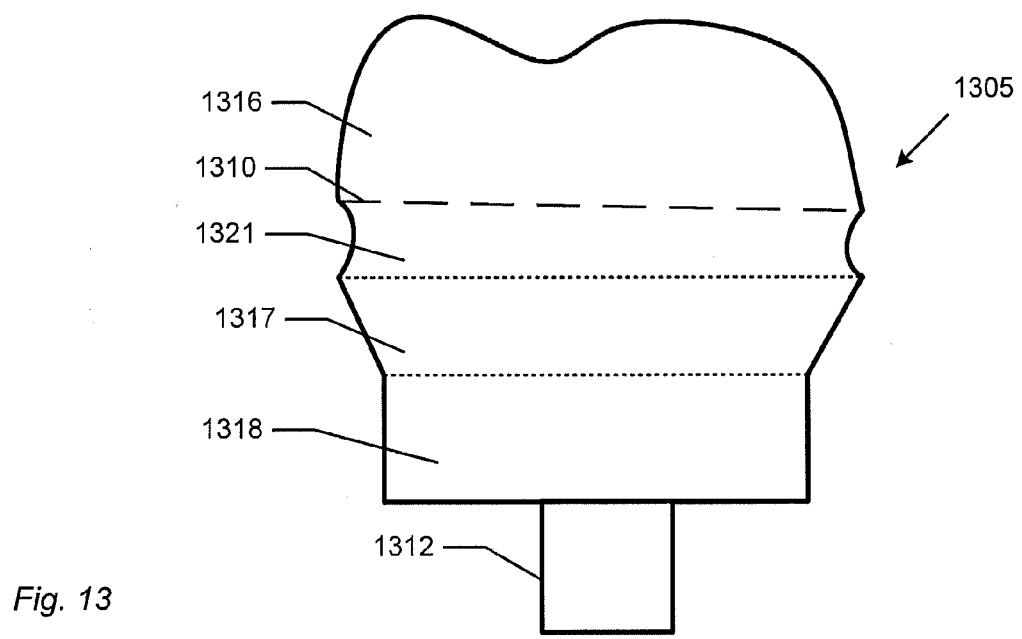
FIG. 13 shows an example of a removable component.

FIG. 13 shows an example of a removable component.

The removable component 1305 comprises an anatomical layer 1316, a margin line layer 1310, a ditch layer 1321, a connection layer 1317 and a base or bottom layer 1318.

The ditch layer 1321 is optional, but the advantage of providing a ditch layer 1321 between the margin line layer 1310 and the connection layer 1317 is for providing workspace for the dental technician on the removable component 1305.

Furthermore, a pin 1312 may be arranged under the base layer 1318.

FIG. 14 shows an example of a cavity of a model and a removable component with non-straight sides.

FIG. 14a) shows that the cavity 1407 of the model 1401 is formed as stairs 1422, and FIG. 14b) shows that the bottom part of the removable component 1405 is formed as corresponding stairs 1422. The stairs are overall non-straight, but the single steps of the stairs may be straight. The size of the stairs may be much smaller than shown here, they may be so small that they can no be seen with the naked eye. If there are many stairs, then the overall visual impression will be that the side is actually sloping.

It is optional whether the bottom of the cavity is closed or open, which is indicated with a broken line.

FIG. 15 shows an example of a cavity of a model and a removable component with non-straight sides.

FIG. 15a) shows that the cavity 1507 of the model 1501 is formed as stairs 1522, and FIG. 15b) shows that the bottom part of the removable component 1505 is formed as corresponding stairs 1522. The stairs are overall non-straight, but the single steps of the stairs may be straight.

The removable component 1505 comprises a pin 1512, which is shown to be so long that it extends all the way through the model 1501. It is optional whether the bottom of the hole in the model 1501 for the pin 1512 is closed or open, which is indicated with a broken line.

Figure 16A:
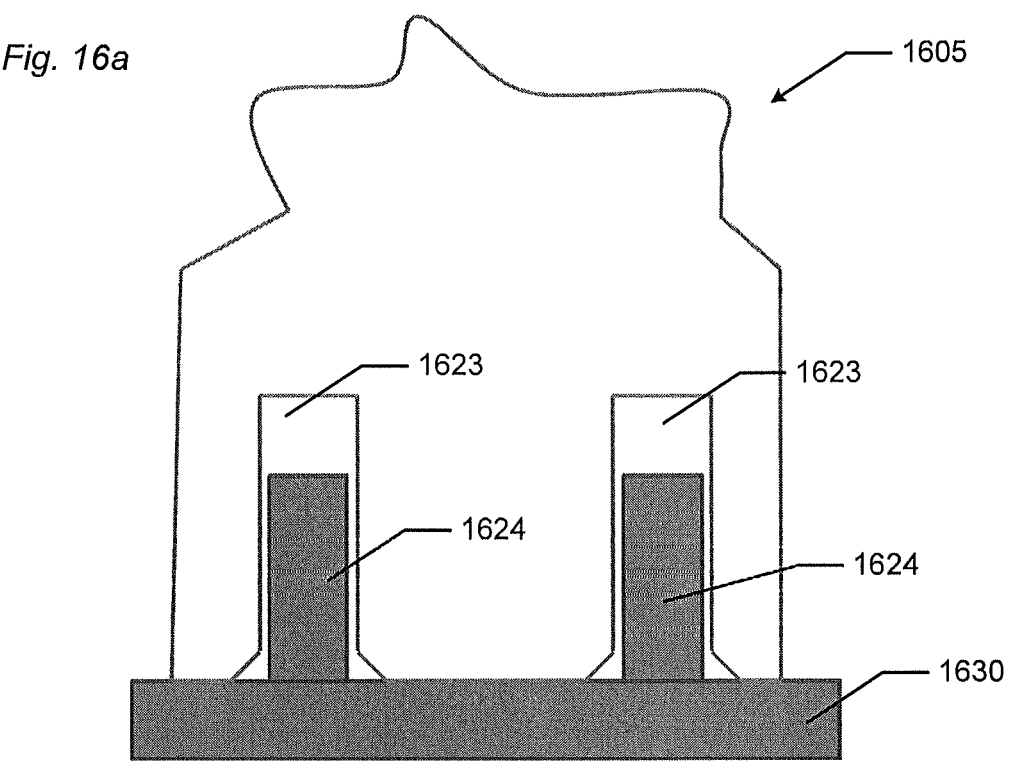
FIG. 16 shows an example of removable components with indentations.
Figure 16B:
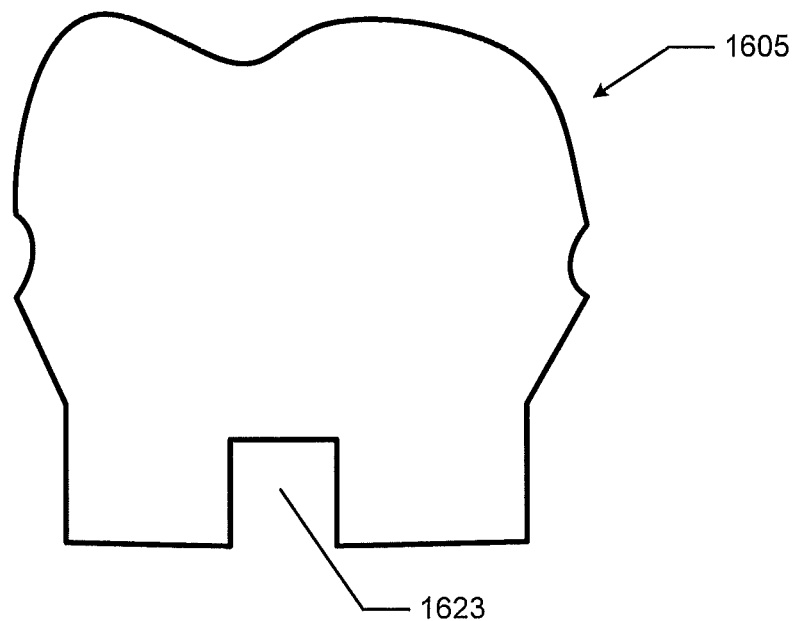

FIG. 16 shows an example of removable components with indentations.

FIG. 16a)-b) shows that instead of e.g. cavities in the model, the removable component 1605 can have indentations 1623 which facilitates the support and positioning of the removable component 1605 in the model, where the model may be in the form of a mounting base 1630. The mounting base 1630 may be a standard or generic mounting base or a specific mounting base for the specific patient case.

FIG. 16a) furthermore shows that the mounting base 1630 can have protrusions 1624 which fits into the indentations 1623 of the removable component 1605.

FIG. 17 shows an example of moving the gingiva around the removable component.

Figure 17A:
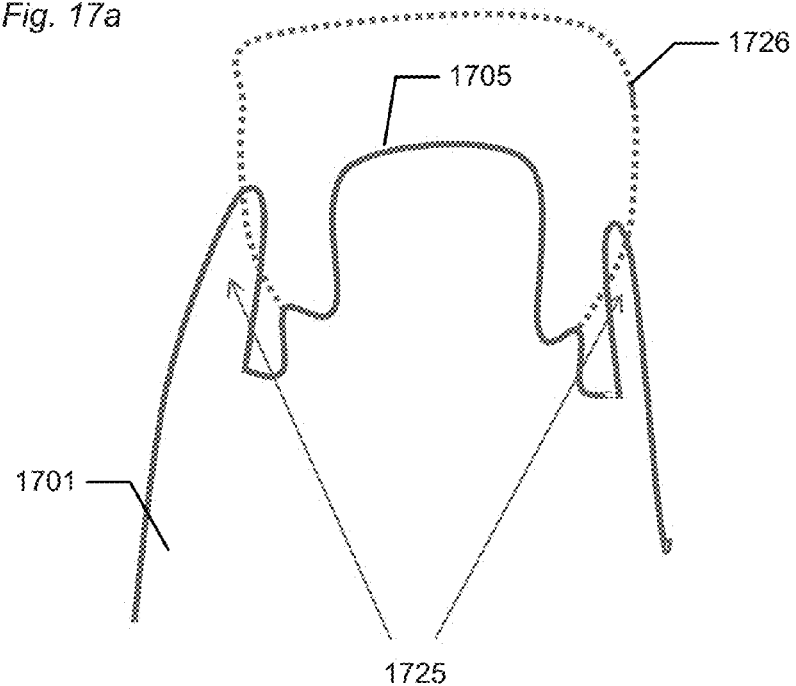
FIG. 17 shows an example of moving the gingival part of the model around the removable component.

FIG. 17a) shows the model 1701 before a portion of the gingiva 1725 of the model has been repositioned.

Figure 17B:
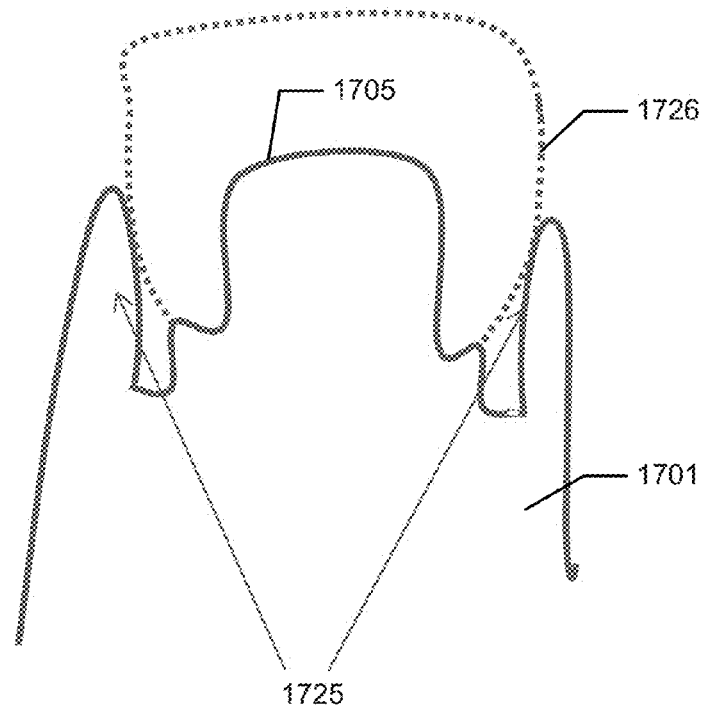

FIG. 17b) shows the model 1701 after a portion of the gingiva 1725 of the model has been repositioned. After the gingiva part 1725 has been moved, the model 1701 can be manufactured.

When a tooth is prepared in the mouth of the patient, so much of the tooth may be grinded away, that the soft, compliant gingival tissue around the prepared tooth will adjoin or follow or collapse to follow the new reduced shape of the prepared tooth instead of remaining in the original shape following the original non-prepared tooth. When digitally repositioning, removing, or relocating the gingival part 1725 of the model 1701 around the removable component 1705 then there is space for a restoration 1726 and veneering.

The gingival part 1725 of the model 1701 is moved outwards relative to the removable component 1705, i.e. away from the removable component, and it is moved without changing the size of gingival part 1725, only the shape of the gingival part 1725 is changed.

If the restoration 1726 is designed using CAD, it can be derived from the CAD program how much the gingival part 1725 on the model 1701 should be moved in order to fit the modeled restoration 1726.

In FIG. 17, the removable component 1705 is not shown as a removable component but as a fixed part of the model 1701 and thus the component 1705 could be denoted a tooth or die in this case.

Figure 18:
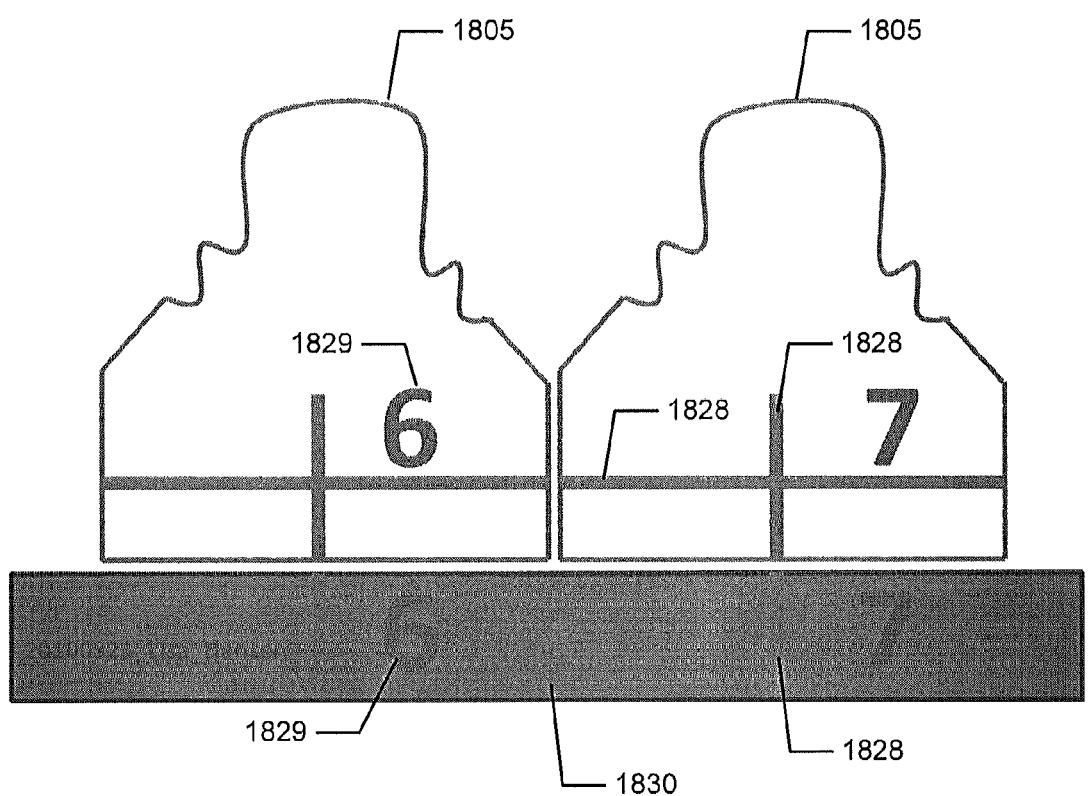
FIG. 18 shows an example of visual guidelines on the removable component and gingival part of the model.

FIG. 18 shows an example of visual guidelines on the removable component and mounting base.

Visual guidelines 1828 may be provided for facilitating a correct arrangement of the removable component 1805 relative to the model or mounting base 1830. A mounting base 1830 is shown here, because the removable component 1805 is shown to be a stand-alone component and not a component to be arranged in a cavity of a model, however, visual guidelines may of course also be arranged on a model with cavities for the removable component. The mounting base 1830 may be a standard or generic mounting base or a specific mounting base for the specific patient case.

The visual guidelines 1828 are straight lines which are present on both the removable components 1805 and on the mounting base 1830. When the removable component 1805 is arranged correctly relative to the mounting base 1830, then the visual guidelines 1828 on the removable component 1805 and the mounting base 1830 match, meet, or fit together.

The visual guidelines 1828 may be printed, embossed etc., and may e.g. be grooves or elevations.

Furthermore, corresponding numbers 1829, here number 6, are arranged on the removable component 1805 and on the mounting base 1830 for keeping track of where the different removable components 1805 should be arranged in the mounting base 1830, when there are more removable components 1805 which could be difficult to distinguish from each other.

Although some embodiments have been described and shown in detail, the invention is not restricted to them, but may also be embodied in other ways within the scope of the subject matter defined in the following claims. In particular, it is to be understood that other embodiments may be utilised and structural and functional modifications may be made without departing from the scope of the present invention.

In device claims enumerating several means, several of these means can be embodied by one and the same item of hardware. The mere fact that certain measures are recited in mutually different dependent claims or described in different embodiments does not indicate that a combination of these measures cannot be used to advantage.

It should be emphasized that the term "comprises/comprising" when used in this specification is taken to specify the presence of stated features, integers, steps or components but does not preclude the presence or addition of one or more other features, integers, steps, components or groups thereof.

It should be emphasized that the term "according to any of the preceding claims" may be interpreted as meaning "according to any one or more of the preceding claims", such that the limitations of one or several dependent claims may be read into an independent claim.

The features of the method described above and in the following may be implemented in software and carried out on a data processing system or other processing means caused by the execution of computer-executable instructions. The instructions may be program code means loaded in a memory, such as a RAM, from a storage medium or from another computer via a computer network. Alternatively, the described features may be implemented by hard-wired circuitry instead of software or in combination with software.

The invention claimed is:

1. A method of generating a virtual model of a set of teeth for manufacturing a physical model of the set of teeth, where the generated virtual model is configured such that at least one tooth is part of a removable component of the virtual model, the method comprising:
    obtaining a virtual model of the set of teeth, the virtual model comprising a gingival part and the at least one tooth which is part of the removable component in the virtual model, the at least one tooth being removable in a longitudinal direction of the at least one tooth;
    generating a cavity in said gingival part, said cavity comprising a cavity wall, into which cavity the removable component fits such that an interface between the removable component and the cavity wall is defined, where the removable component and the cavity are configured to provide a gap at said interface, the gap extending circumferentially about a portion of the removable component in a direction perpendicular to the longitudinal direction; and
    providing supporting elements configured for supporting and positioning the removable component in the cavity, where the supporting elements extend in the longitudinal direction on one of said removable component and said cavity wall such that the supporting elements extend across said gap between said removable component and said cavity wall, such that in the physical model manufactured from the virtual model, the supporting elements support and position the removable component in the cavity;
    wherein, in at least one cross section taken through the removable component and the gap in a direction perpendicular to the longitudinal direction, contact between the removable component and the cavity wall at said interface is provided only by surfaces of the supporting elements and the other of the removable component and the cavity wall such that, in the at least one cross section, the gap extends only between the surfaces of the supporting elements.

2. The method according to claim 1, wherein at least part of said supporting elements are generated on the removable component such that an area of contact between the removable component and the cavity wall at said interface is controlled by a shape of adjoining surfaces of the supporting elements and the cavity wall.

3. The method according to claim 1, wherein at least part of said supporting elements are generated on the cavity wall such that an area of contact between the removable component and the cavity wall at said interface is controlled by a shape of adjoining surfaces of the supporting elements and the removable component.

4. The method according to claim 1, wherein the supporting elements comprise one or more friction points providing friction between the removable component and the cavity.

5. The method according to claim 1, wherein the supporting elements are arranged in positions corresponding to each straight side of a base of the removable component.

6. The method according to claim 1, wherein a width of said supporting element in an area of contact between the supporting elements and the other of the removable component and the cavity wall is in the range of 0.01 mm to 4 mm.

7. The method according to claim 1, wherein a length of said supporting element in an area of contact between the supporting elements and the other of the removable component and the cavity wall is in the range of 0.01 mm to 20 mm.

8. The method according to claim 1, wherein the height of the supporting elements is in the range of 0.05 mm to 2 mm.

9. The method according to claim 1, wherein a number $N_{elem}$ of supporting elements are provided on the removable component and/or the cavity wall, where $N_{elem}$ is selected from the group of 3, 4, 6, 8, 9, 10, 12 or 16.

10. The method according to claim 1, wherein a ratio between an area of contact between the supporting elements and the other of the removable component and the cavity wall and an area of said cavity wall or a ratio between the area of contact and an area of said interface is below 0.9.

11. The method according to claim 1, wherein the supporting elements are formed as cut-off pyramids or as square frusta or rectangular frusta.

12. The method according to claim 1, wherein the supporting elements are configured to provide that their volume overlap at least partly with a volume of the removable component or the cavity wall when the removable component is arranged in the cavity, such that a tight fit is created between the cavity and the removable component.

13. The method according to claim 1, where a contour of the cavity wall follows an outer curve and the contour of the removable component follows an inner curve, where the inner curve is arranged inside the outer curve.

14. The method according to claim 13, wherein supporting elements generated on said removable component comprise a surface in an area of contact between the supporting elements and the other of the removable component and the cavity wall, which surface is aligned with the outer curve, such that these supporting elements are shaped to have a surface in the area of contact which is parallel to a surface of the cavity wall at the area of contact.

15. The method according to claim 13, wherein supporting elements are generated on the wall of said cavity and comprise a surface in an area of contact between the supporting elements and the other of the removable component and the cavity wall, which surface is aligned with the inner curve, such that these supporting elements are shaped to have a surface in the area of contact which is parallel to a surface of the removable component at the area of contact.

16. The method according to claim 1, wherein said providing a virtual model comprises generating said virtual model from a virtual representation of the set of teeth, and wherein the virtual representation of the set of teeth is provided by scanning the set of teeth by means of an intraoral scanner or scanning an impression of the set of teeth.

17. The method according to claim 1, wherein the method comprises digitally repositioning the gingival part of the model around the removable component, before manufacturing the physical model.

18. The method according to claim 17, wherein digitally repositioning the gingival part of the model comprises digitally moving the gingival part of the model away from the removable component.

19. A system for generating a virtual model of a set of teeth for manufacturing a physical model of the set of teeth, where the system comprises a processor configured for:

generating a virtual model of the set of teeth, where the virtual model is based on a virtual representation of the set of teeth;

providing that at least one tooth is configured to be arranged as part of a removable component in the virtual model, where the removable component is adapted to fit into a corresponding cavity in a gingival part of the virtual model such that an interface between the removable component and a wall of the cavity is defined, where the removable component and the cavity are configured to provide a gap at said interface, the at least one tooth being removable in a longitudinal direction of the at least one tooth, and the gap extending circumferentially about a portion of the removable component in a direction perpendicular to the longitudinal direction;

providing supporting elements extending in the longitudinal direction for supporting and positioning the removable component in its corresponding cavity, where the supporting elements are provided on one of said removable component and said cavity wall such that the supporting elements extend across said gap between said removable component and said cavity wall; and configuring the supporting elements such that, in at least one cross section taken through the removable component and the gap in a direction perpendicular to the longitudinal direction, contact between the removable component and the cavity wall at said interface is provided only by surfaces of the supporting elements and the other of the removable component and the cavity wall such that, in the at least one cross section, the gap extends only between the surfaces of the supporting elements.

20. A method of generating a virtual model of a set of teeth for manufacturing a physical model of the set of teeth, where at least one tooth of the manufactured physical model is part of a removable component which is removable in a longitudinal direction of the at least one tooth, the method comprising:

obtaining a virtual model of the set of teeth, the virtual model of the set of teeth comprising a gingival part and the at least one tooth;

generating a virtual model of the removable component comprising the at least one tooth;

generating in said gingival part a cavity comprising a cavity wall, into which cavity the virtual model of the removable component fits with a gap such that an interface between the removable component and the cavity wall is defined, the gap extending circumferentially about a portion of the virtual model of the removable component in a direction perpendicular to the longitudinal direction; and providing virtual supporting elements to the cavity wall, the virtual supporting elements extending in the longitudinal direction, where the supporting elements in the manufactured physical model support and position the removable component in the cavity, and in at least one cross section taken through the removable component and the gap in a direction perpendicular to the longitudinal direction, contact between the removable component and the cavity wall at said interface is provided only by surfaces of the supporting elements and the removable component such that, in the at least one cross section, the gap extends only between the surfaces of the supporting elements.

21. A method of generating a virtual model of a set of teeth for manufacturing a physical model of the set of teeth, where at least one tooth of the manufactured physical model is part of a removable component which is removable in a longitudinal direction of the at least one tooth, the method comprising:

obtaining a virtual model of the set of teeth, the virtual model of the set of teeth comprising a gingival part and the at least one tooth;

generating a virtual model of the removable component comprising the at least one tooth;

generating in said gingival part a cavity comprising a cavity wall, into which cavity the virtual model of the removable component fits with a gap such that an interface between the removable component and the cavity wall is defined, the gap extending circumferentially about a portion of the virtual model of the removable component in a direction perpendicular to the longitudinal direction; and providing virtual supporting elements to the portion of the removal component at the interface, the virtual supporting elements extending in the longitudinal direction, where the supporting elements in the manufactured physical model support and position the removable component in the cavity, and in at least one cross section taken through the removable component and the gap in a direction perpendicular to the longitudinal direction, contact between the removable component and the cavity wall at said interface is provided only by surfaces of the supporting elements and the cavity wall such that, in the at least one cross section, the gap extends only between the surfaces of the supporting elements.

22. A method of generating a virtual model of a set of teeth for manufacturing a physical model of the set of teeth, where at least one tooth of the manufactured physical model is part of a removable component which is removable in a longitudinal direction of the at least one tooth, the method comprising executing computer program code on a data processing system, where the computer program code when executed causes the data processing system to:

obtain a virtual model of the set of teeth;

generate a virtual model of the removable component from the virtual model of the set of teeth, where the virtual model of the removable component comprises the at least one tooth;

generate a cavity in the virtual model of the set of teeth, the cavity comprising a cavity wall;

where the virtual model of the removable component fits into the cavity with a gap between the removable component and the cavity wall, the gap extending circumferentially about a portion of the virtual model of the removable component in a direction perpendicular to the longitudinal direction; and generating one or more supporting elements on the virtual model of the removable component and/or on the cavity wall, said supporting elements extending across the gap such that contact between the removable component and the cavity wall at said interface is provided only by the supporting elements such that, in the at least one cross section, the gap extends only between the supporting elements.

* * * * *